United States Patent [19]

Petersen et al.

[11] Patent Number: 5,453,422
[45] Date of Patent: Sep. 26, 1995

[54] QUINOLONE- AND NAPHTHYRIDONE CARBOXYLIC ACID DERIVATIVES, PROCESS FOR THEIR PRODUCTION, ANTIBACTERIAL COMPOSITIONS AND FEED ADDITIVES CONTAINING THEM

[75] Inventors: Uwe Petersen, Leverkusen; Thomas Schenke, Bergisch Gladbach; Klaus Grohe; Michael Schriewer, both of Odenthal; Ingo Haller, Wuppertal; Karl G. Metzger, Wuppertal; Rainer Endermann, Wuppertal; Hans-Joachim Zeiler, Velbert, all of Germany

[73] Assignee: Bayer Aktiengesellschaft, Leverkusen, Germany

[21] Appl. No.: 151,603

[22] Filed: Nov. 12, 1993

Related U.S. Application Data

[62] Division of Ser. No. 931,746, Aug. 18, 1992, Pat. No. 5,284,842, which is a division of Ser. No. 699,880, May 14, 1991, Pat. No. 5,173,484, which is a continuation-in-part of Ser. No. 298,459, Jan. 18, 1989, abandoned.

[30] Foreign Application Priority Data

Feb. 5, 1988 [DE] Germany .................. 38 02 478.6
Apr. 29, 1988 [DE] Germany .................. 38 14 517.0

[51] Int. Cl.⁶ .................. A61K 31/47; C07D 401/04
[52] U.S. Cl. .................. 514/187; 514/312; 546/5; 546/156
[58] Field of Search .................. 546/156, 5; 514/312, 514/187

[56] References Cited

U.S. PATENT DOCUMENTS

| | | | |
|---|---|---|---|
| 4,382,892 | 5/1983 | Hayakawa et al. | 544/101 |
| 4,508,724 | 4/1985 | Taylor, Jr. et al. | 514/317 |
| 4,556,658 | 12/1985 | Grohe et al. | 514/254 |

(List continued on next page.)

FOREIGN PATENT DOCUMENTS 0275971  7/1988  European Pat. Off. .

OTHER PUBLICATIONS

Grohe et al., *Chemical Abstracts*, vol. 102, No. 78744 (1984).
Grohe et al., *Chemical Abstracts*, vol. 101 No. 211165 (1984).
Balsamo et al. J. Med. Chem., 30, pp. 222–225 (1987).
Averbach et al. Tetrahedron Letters No. 46, pp. 4561–4564 (1973).
Giustiniani Gazz. Chim. Ital. 24, pp. 223–229 (1894).
Vasileva Zh, Org. Khim, 14, (7), 1420 (1978) English translation.
Jacobsen et al. Acta Chemica Scandinavica B 34 (1980), pp. 319–326.
Viscontini et al. Helv. Chim. Acta, 50, 1967, pp. 1289–1293.
Gassman et al. J. Amer. Chem. Soc., 104, 1982, pp. 5849–5850.
Wu et al., J. Med. Pharm. Chem., 5, 1962, pp. 752–762.
Domagala et al. J. Med. Chem., 31, 1988, pp. 503–506.

*Primary Examiner*—Emily Bernhardt
*Attorney, Agent, or Firm*—Sprung Horn Kramer & Woods

[57] ABSTRACT

An antibacterially active quinolone or naphthyridonecarboxylic acid derivative of the formula

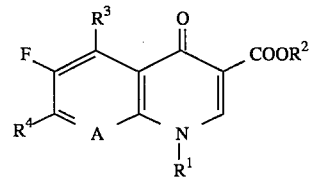

in which
  $R^1$ stands for various organic radical,
  $R^2$ stands for hydrogen, alkyl having 1 to 4 carbon atoms or (5-methyl-2-oxo-1,3-dioxol-4-yl)-methyl,
  $R^3$ stands for hydrogen or amino,
  $R^4$ stands for a radical of the formula

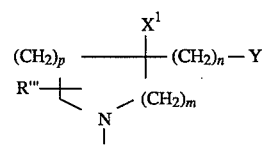

or

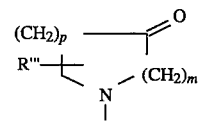

and
A stands for N or C—$R^5$,
wherein
  $R^5$ stands for hydrogen, halogen methyl, cyano or nitro or else together with $R^1$ can form a bridge of the structure

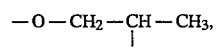

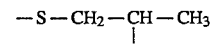

or

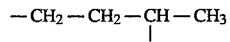

or a pharmaceutically utilizable hydrate, acid addition salt, alkali metal salt, alkaline earth metal salt, silver salt or guanidinium salt of the carboxylic acid when $R^2$ is hydrogen.

11 Claims, No Drawings

U.S. PATENT DOCUMENTS

| | | | |
|---|---|---|---|
| 4,616,019 | 10/1986 | Chu | 514/254 |
| 4,638,067 | 1/1987 | Culbertson et al. | 546/15 |
| 4,649,144 | 3/1987 | Matsumoto et al. | 514/300 |
| 4,665,079 | 5/1987 | Culbertson et al. | 514/312 |
| 4,666,920 | 5/1987 | Grohe et al. | 514/312 |
| 4,730,000 | 3/1988 | Chu | 544/363 |
| 4,735,944 | 4/1988 | Bollinger | 514/278 |
| 4,753,925 | 6/1988 | Grohe et al. | 514/254 |
| 4,771,054 | 9/1988 | Domagala et al. | 514/312 |
| 4,771,055 | 9/1988 | Domagala et al. | 514/312 |
| 4,774,246 | 9/1988 | Chu | 514/254 |
| 4,777,175 | 10/1988 | Culbertson | 514/300 |
| 4,822,801 | 4/1989 | Domagala et al. | 514/312 |
| 4,886,810 | 12/1989 | Matsumoto et al. | 514/312 |
| 4,920,120 | 4/1990 | Domagala et al. | 546/156 |
| 4,927,926 | 5/1990 | Corominas et al. | 544/101 |
| 4,952,695 | 8/1990 | Groche et al. | 546/156 |
| 4,962,112 | 10/1990 | Rosen et al. | 514/300 |
| 4,997,943 | 3/1991 | Iwata et al. | 546/156 |
| 5,039,683 | 8/1991 | Nakanishi | 514/312 |
| 5,173,484 | 12/1992 | Petersen et al. | 514/187 |

QUINOLONE- AND NAPHTHYRIDONE CARBOXYLIC ACID DERIVATIVES, PROCESS FOR THEIR PRODUCTION, ANTIBACTERIAL COMPOSITIONS AND FEED ADDITIVES CONTAINING THEM

This application is a division of application Ser. No. 07/931,746, filed Aug. 18, 1992, now U.S. Pat. No. 5,284,842, which is a division of application Ser. No. 07/699,880, filed May 14, 1991, now U.S. Pat. No. 5,173,484, which is a continuation-in-part of application Ser. No. 07/298,459, filed Jan. 18, 1989, now abandoned.

The invention relates to quinolone- and naphthyridonecarboxylic acid derivatives which are substituted in the 7-position by a cyclic amine radical which carries a quaternary carbon atom, processes for their preparation, and antibacterial agents and feed additives containing them.

It has been found that quinolone- and naphthyridonecarboxylic acid derivatives of the formula (I)

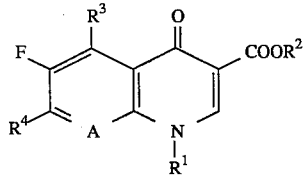

in which $R^1$ stands for methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl or 2,4-difluorophenyl, $R^2$ stands for hydrogen, alkyl having 1 to 4 carbon atoms or (5-methyl-2-oxo-1,3-dioxol-4-yl)-methyl, $R^3$ stands for hydrogen or amino, $R^4$ stands for a radical of the formula

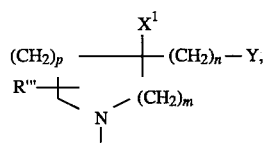

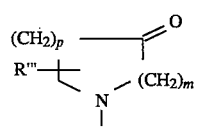

or

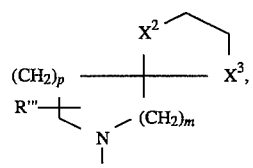

excluding 3-amino-3-methyl-1-pyrrolidinyl,
wherein
p stands for 0, 1 or 2,
m stands for 1 or 2, where p+m together can be 1, 2 or 3,
n stands for 1 or 2, Y stands for

OR, SR, halogen or hydrogen, $X^1$ stands for

OR, SR, halogen, CN, $CONH_2$, COOH or $C_1$–$C_4$-alkyl, $X^2$ and $X^3$ can be identical or different and stand for oxygen, sulphur, NH or N—$CH_3$, R stands for hydrogen, $C_1$–$C_3$-alkyl or $C_1$–$C_3$-acyl, R' stands for hydrogen, $C_1$–C3-alkyl, allyl or propargyl and R" stands for hydrogen, $C_1$–$C_3$-alkyl or $C_3$–$C_6$-cycloalkyl, where R'+R" together can also denote the groups —$CH_2CH_2$—O—$CH_2CH_2$— or —$(CH_2)_k$—, in which k can stand for 3, 4 or 5, R''' stands for hydrogen or $C_1$–$C_3$-alkyl, A stands for N or C—$R^5$, wherein $R^5$ stands for hydrogen, halogen such as fluorine or chlorine, methyl, cyano or nitro or else together with $R^1$ can form a bridge of the structure

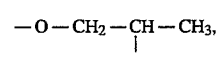

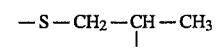

or

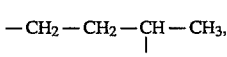

and their pharmaceutically utilizable hydrates and acid addition salts and also the alkali metal salts, alkaline earth metal salts, silver salts and guanidinium salts of the underlying carboxylic acids, have a high antibacterial action, in particular in the gram-positive range.

They are therefore suitable as active compounds for human and veterinary medicine, the treatment of fish for the therapy or prophylaxis of bacterial infections being included in the term veterinary medicine.

Preferred compounds of the formula (I) are those in which $R^1$ stands for ethyl, isopropyl, cyclopropyl, vinyl, 2-hydroxyethyl, 2-fluoroethyl, amino, methylamino, phenyl, 4-fluorophenyl or 2,4-difluorophenyl, $R^2$ stands for hydrogen, alkyl having 1 to 3 carbon atoms or (5-methyl-2-oxo-1,3-dioxol-4-yl)-methyl, $R_3$ stands for hydrogen or amino, $R^4$ stands for a radical of the formula

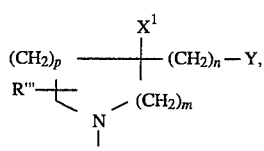

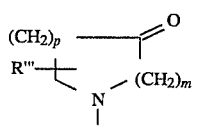

or

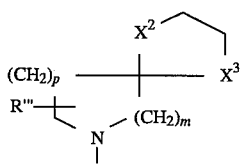

excluding 3-amino-3-methyl-1-pyrrolidinyl,
wherein
p stands for 0, 1 or 2,
m stands for 1 or 2, where p+m together can be 1, 2 or 3,
n stands for 1 or 2,
Y stands for

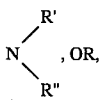, OR, or hydrogen,
$X^1$ stands for

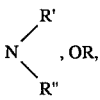, OR, fluorine, chlorine or $C_1$–$C_2$-alkyl,
$X^2$ and $X^3$ can be identical or different and stand for oxygen, sulphur or N—$CH_3$,
R stands for hydrogen, $C_1$–$C_2$-alkyl or acetyl,
R' stands for hydrogen or $C_1$–$C_2$-alkyl, and
R" stands for hydrogen or $C_1$–$C_2$-alkyl,
where
R'+R" together also denote the groups —$CH_2CH_2$—O—$CH_2CH_2$— or —$(CH_2)_k$—, in which k can stand for 3, 4 or 5,
R''' stands for hydrogen or $C_1$–$C_2$-alkyl and
A stands for N or C—$R^5$,
wherein
$R^5$ stands for hydrogen, halogen such as fluorine or chlorine or methyl or else together with $R^1$ can form a bridge of the structure

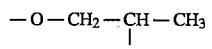

or

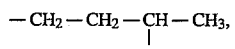

and their pharmaceutically utilizable hydrates and acid addition salts and also the alkali metal salts, alkaline earth metal salts, silver salts and guanidinium salts.

Particularly preferred compounds of the formula (I) are those in which
$R^1$ stands for ethyl, isopropyl, cyclopropyl, vinyl, 2-hydroxyethyl, 2-fluoroethyl, amino, methylamino, phenyl, 4-fluorophenyl or 2,4-difluorophenyl,
$R^2$ stands for hydrogen or alkyl having 1 or 2 carbon atoms,
$R^3$ stands for hydrogen,
$R^4$ stands for a radical of the formula

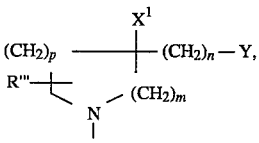

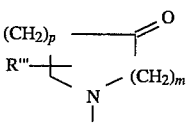

or

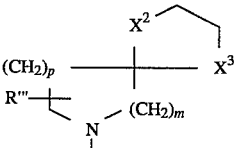
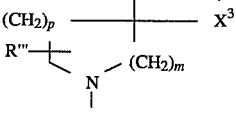

excluding 3-amino-3-methyl-1-pyrrolidinyl,
wherein
p stands for 0, 1 or 2,
m stands for 1 or 2, where p+m together can be 1, 2 or 3,
n stands for 1,
Y stands for

OR, or hydrogen,
$X^1$ stands for

OR, chlorine or methyl,

X² and X³ can be identical or different and stand for oxygen or N—CH₃,

R stands for hydrogen or methyl,

R' stands for hydrogen or methyl,

R" stands for hydrogen or methyl,

R'" stands for hydrogen or methyl and

A stands for N or C—R⁵, wherein

R⁵ stands for hydrogen, halogen, such as fluorine or chlorine or else together with R¹ can form a bridge of the structure

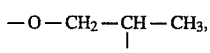

and their pharmaceutically utilizable hydrates and acid addition salts and also the alkali metal salts, alkaline earth metal salts, silver salts and guanidinium salts.

Furthermore, it has been found that the compounds of the formula (I) are obtained when compounds of the formula (II)

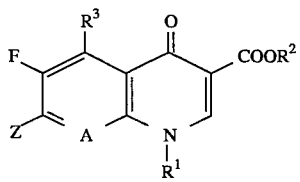

in which

Z stands for fluorine or chlorine and

R¹, R², R³ and A have the abovementioned meaning, are reacted with compounds of the formula (III)

 (III)

in which

R⁴ has the abovementioned meaning, if appropriate in the presence of acid entrainers.

Compounds of the structure (Ia)

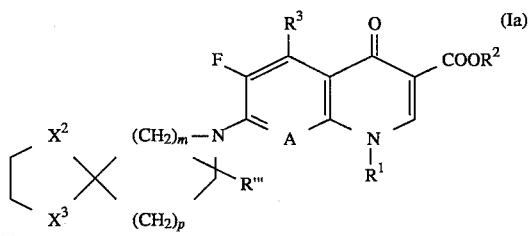

in which

R¹, R², R³, R'", A, X², X³, m and p have the abovementioned meaning, can also be prepared by reaction of a compound of the formula (IV)

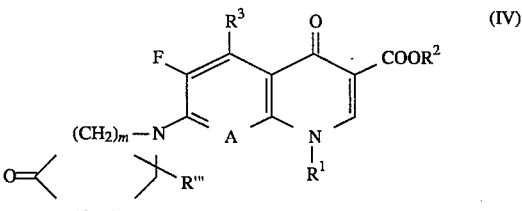

in which

R¹, R², R³, R'", A, m and P have the abovementioned meaning, with a compound of the formula (V)

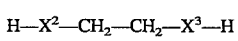 (V)

in which

X² and X³ have the abovementioned meaning.

If, for example, 8-chloro-1-cyclopropyl-6,7-difluoro-1,4-dihydro-4-oxo-3-quinolinecarboxylic acid and 3-ethylaminomethyl-3-hydroxy-pyrrolidine are used as starting substances, then the course of the reaction can be represented by the following equation:

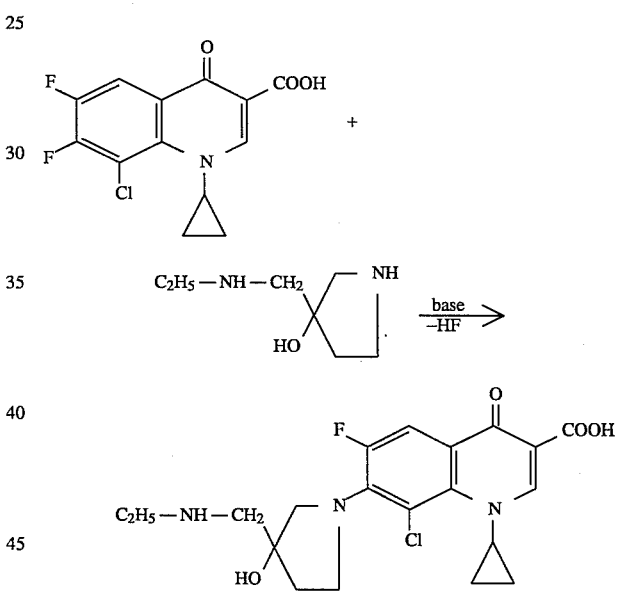

The compounds of the formula (II) used as starting substances are known or can be prepared by known methods. Examples which may be mentioned are:

7-chloro-1-cyclopropyl-6-fluoro-1,4-dihydro-4-oxo-3-quinolinecarboxylic acid (German Patent Application 3,142,854), 1-cyclopropyl-6,7-difluoro-1,4-dihydro-4-oxo-3-quinolinecarboxylic acid (European Patent Application 113,091), 8-chloro-1-cyclopropyl-6,7-difluoro-1,4-dihydro-4-oxo-3-quinolinecarboxylic acid (German Patent Application 3,420,743), 1-cyclopropyl-6,7,8-trifluoro-1,4-dihydro-4-oxo-3-quinolinecarboxylic acid (German Patent Application 3,318,145), 1-cyclopropyl-6,7-difluoro-1,4-dihydro-8-methyl-4-oxo-3-quinolinecarboxylic acid, 6,7-difluoro-1-ethyl-1,4-dihydro-4-oxo-3-quinolinecarboxylic acid, 7-chloro-6-fluoro-1-ethyl-1,4-dihydro-4-oxo-3-quinolinecarboxylic acid, 7-chloro-6-fluoro-1,4-dihydro-1-(2-hydroxyethyl)-4-oxo-3-quinolinecarboxylic acid, 1-cyclopropyl-7-chloro-6-fluoro-1,4-dihydro-8-nitro-4-oxo-3-quinolinecarboxylic acid, 6,7-difluoro-1-(2-fluoroethyl)-1,4-dihydro-4-oxo-3-quinolinecarboxylic acid, 6,7-difluoro-1,4-dihydro-1-methoxy-4-oxo-3-quinolinecarboxylic acid, 6,7-difluoro-1,4-dihydro-1-methylamino-4-oxo-3-quinolinecarboxylic acid, 6,7-difluoro-1,4-dihydro-4-oxo-1-phenyl-3-quinolinecarboxylic acid, 6,7-difluoro-1-(4-fluoro-phenyl)-1,4-dihydro-4-oxo-3-quinolinecarboxylic acid, 6,7-difluoro-1-(3,4-difluoro-phenyl)-1,4-dihydro-4-oxo-3-quinolinecarboxylic acid, 7-chloro-1-cyclopropyl-6-fluoro-1,4-dihydro-4-oxo-1,8-naphthyridine-3-carboxylic acid, ethyl 1-cyclopropyl-6,7,8-trifluoro-1,4-dihydro-4-oxo-3-quino-linecarboxylate (German Patent Application 3,318,145), 9,10-difluoro-2,3-dihydro-3-methyl-7-oxo-7H-pyrido[1,2,3-de][1,4]benzoxacine-6-carboxylic acid (European Patent Application 47,005), 8,9-difluoro-6,7-dihydro-5-methyl-1-oxo-1H,5H-benzo[i,j]quinolicine-2-carboxylic acid, 7-chloro-6-fluoro-1-phenyl-1,4-dihydro-4-oxo-1,8-naphthyridine-3-carboxylic acid (European Patent Application 53,580), 7-chloro-6-fluoro-1-(4-fluorophenyl)-1,4-dihydro-4-oxo-1,8-naphthyridine-3-carboxylic acid (European Patent Application 153,580), 6,7,8-trifluoro-1,4-dihydro-1-methylamino-4-oxo-3-quinolinecarboxylic acid (German Patent Application 3,409,922), 1-amino-6,7,8-trifluoro-1,4-dihydro-4-oxo-3-quinolinecarboxylic acid (German Patent Application 3,409,922), 6,7,8-trifluoro-1,4-dihydro-1-dimethylamino-4-oxo-3-quinolinecarboxylic acid (German Patent Application 3,409,922), 7-chloro-6-fluoro-1,4-dihydro-8-nitro-4-oxo-1-phenyl-3-quinolinecarboxylic acid, 7-chloro-6-fluoro-1-(4-fluorophenyl)-1,4-dihydro-8-nitro-4-oxo-3-quinolinecarboxylic acid, 6,7-difluoro-1-(4-fluorophenyl)-1,4-dihydro-8-methyl-4-oxo-3-quinolinecarboxylic acid, 6-chloro-7-fluoro-1-(4-fluorophenyl)-1,4-dihydro-4-oxo-3-quinolinecarboxylic acid (European Patent Application 131,839), 6-chloro-7-fluoro-1-(2,4-difluorophenyl)-1,4-dihydro-4-oxo-3-quinolinecarboxylic acid (European Patent Application 131,839), 6,7,8-trifluoro-1-(4-fluorophenyl)-1,4-dihydro-4-oxo-3-quinolinecarboxylic acid (European Patent Application 154,780), 6,7,8-trifluoro-1-(2,4-difluorophenyl)-1,4-dihydro-4-oxo-3-quinolinecarboxylic acid (European Patent Application 154,780), 6,7,8-trifluoro-1,4-dihydro-4-oxo-1-phenyl-3-quinolinecarboxylic acid (European Patent Application 154,780), 7-chloro-1-ethyl-6-fluoro-1,4-dihydro-4-oxo-1,8-naphthyridine-3-carboxylic acid, 6,7-difluoro-1,4-dihydro-4-oxo-1-vinyl-3-quinolinecarboxylic acid.

The compounds of the formula (III) used as starting compounds are in some cases new and therefore an embodiment of the present invention.

Their preparation can be carried out by various processes:

1. Ring-opening to form the hydroxyamines (3) is carried out by reaction of the spiro-oxiranes protected on the nitrogen (1) [J. Med. Chem. 30, 222 (1987); U.S. Pat. No. 4,508,724; EP 189,370] with amines (2). Elimination of the protective group yields starting compounds of the formula (IIIa):

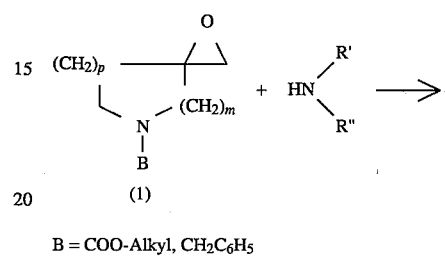

B = COO-Alkyl, $CH_2C_6H_5$

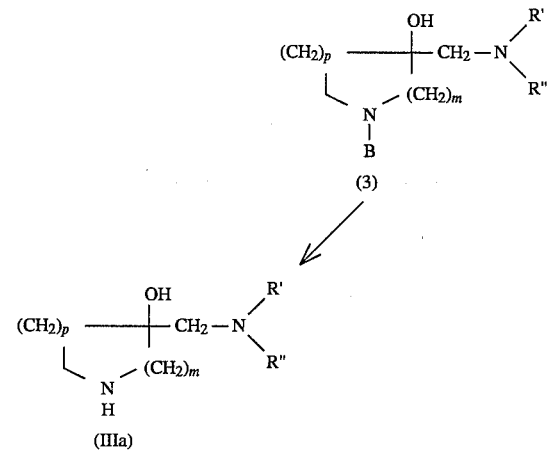

2. The cyclization of the succinic acid ester (4) [Tetrahedron Letters 46, 4561 (1973)] with benzylamine yields the alkyl 1-benzyl-3-hydroxy-5-oxo-pyrrolidine-3-carboxylate (5) which, after reaction with an amine (2), reacts to give the amide (6). Subsequent reduction with $LiAlH_4$ and hydrogenolytic elimination of the benzyl group yields starting compounds of the formula (IIIb):

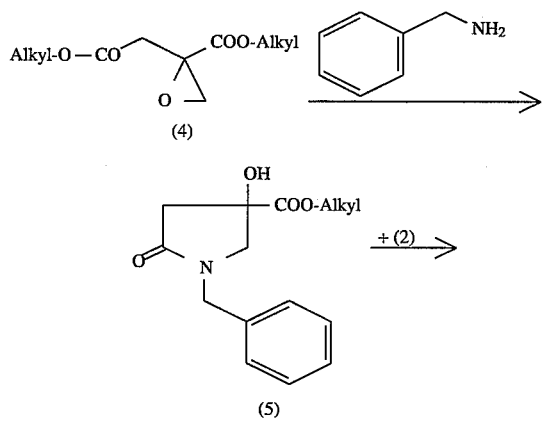

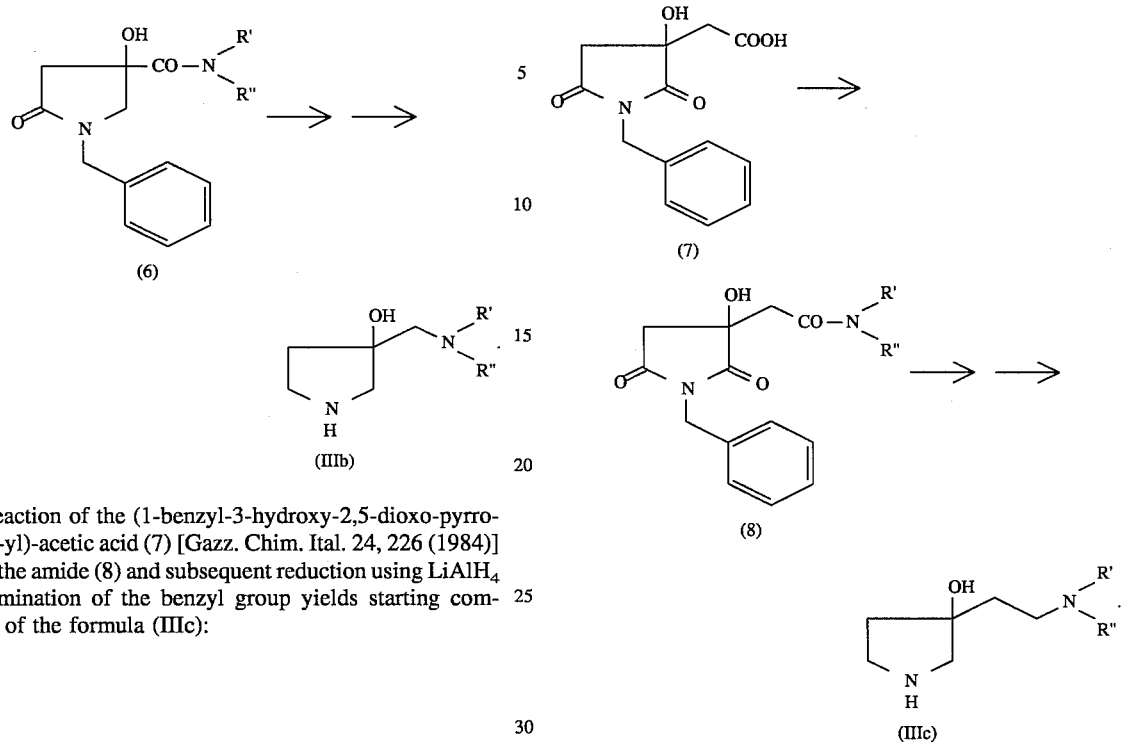

3. Reaction of the (1-benzyl-3-hydroxy-2,5-dioxo-pyrrolidin-3-yl)-acetic acid (7) [Gazz. Chim. Ital. 24, 226 (1984)] to give the amide (8) and subsequent reduction using LiAlH₄ and elimination of the benzyl group yields starting compounds of the formula (IIIc):

4. 3-Hydroxy-3-methyl-pyrrolidine can be prepared by LiAlH₄ reduction of 4-hydroxy-4-methyl-pyrrolidin-2-one [Zh. Org. Khim. 14, 7, p. 1420 (1978)] or by debenzylation of 1-benzyl-3-hydroxy-3-methyl-pyrrolidine (EP 132,845).

5. Starting from cyclic oxoamines (9) which are blocked by a protective group on the nitrogen, starting compounds of the formulae (IIId), (IIIe) and (IIIf) can be synthesized [Acta Chem. Scand. B 34, 319 (1980)].

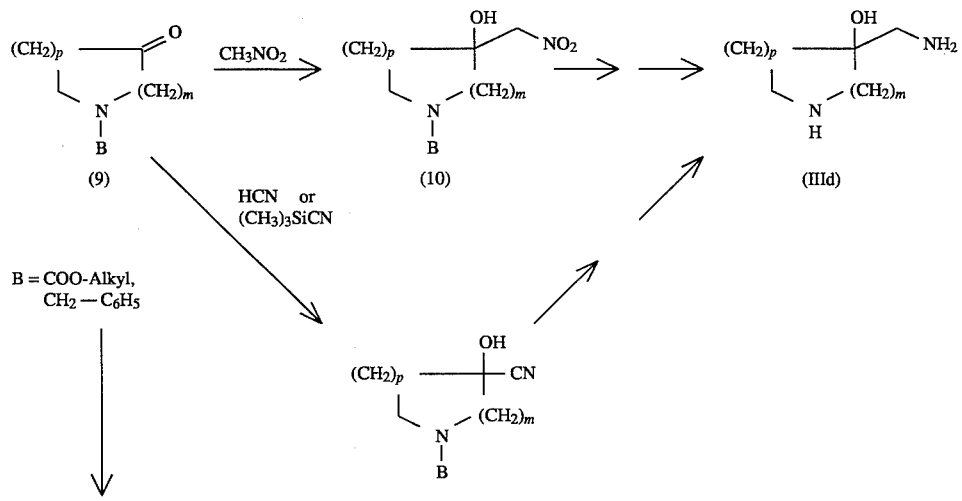

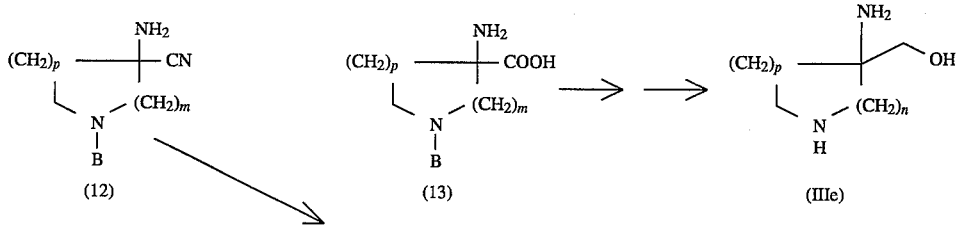

6. The hydroxy group of the hydroxyamines (IIIa)– IIIf) can be alkylated or halogenated.

7. Ketals, thioketals or aminals can be prepared from the cyclic oxoamines (9) [Helv. Chim. Acta 50, 1289 (1967)].

By reaction of the spiro-oxiranes protected on the nitrogen (1) with trimethylsilyl cyanide [J. Amer. Chem. Soc. 104, 5849 (1982)], the isonitriles (14) can be prepared which can be reacted by hydrolyzing and eliminating the protective group to give the starting compounds of the formula (IIIg):

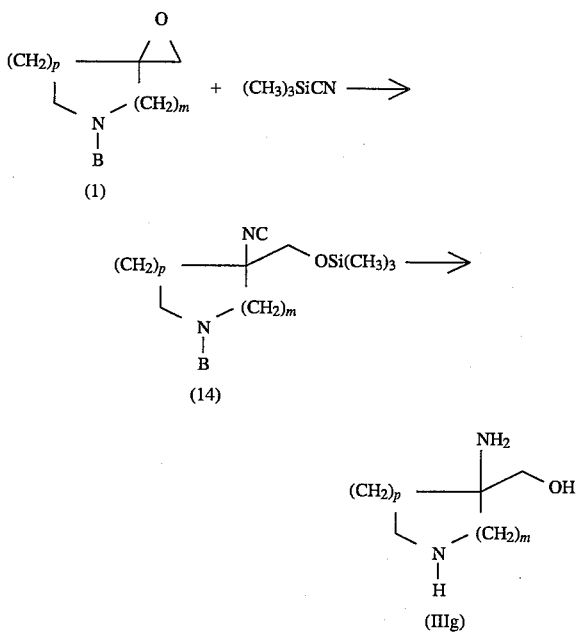

Examples of starting compounds of the formula (III) which may be mentioned are the following compounds, where chiral compounds can be employed both as racemates as well as pure enantiomeric substances:

3-aminomethyl-3-hydroxypyrrolidine,
3-acetylaminomethyl-3-hydroxypyrrolidine,
3-tert.-butoxycarbonylaminomethyl-3-hydroxypyrrolidine,
3-hydroxy-3-methylaminomethylpyrrolidine,
3-ethylaminomethyl-3-hydroxypyrrolidine,
3-hydroxy-3-propylaminomethylpyrrolidine,
3-ethylaminomethyl-3-methoxypyrrolidine,
3-aminomethyl-3-fluoropyrrolidine,
3-aminomethyl-3-chloropyrrolidine,
3-fluoro-3-methylaminomethylpyrrolidine,
3-chloro-3-methylaminomethylpyrrolidine,
3-ethylaminomethyl-3-fluoropyrrolidine,
3-chloro-3-ethylaminomethylpyrrolidine,
3-hydroxy-3-methylpyrrolidine,
3-hydroxy-3-methoxymethylpyrrolidine,
3-methoxy-3-methylaminomethylpyrrolidine,
3-dimethylaminomethyl-3-fluoropyrrolidine,
3-chloro-3-dimethylaminomethylpyrrolidine,
3-fluoromethyl-3-aminopyrrolidine,
3-ethoxy-3-ethylaminomethylpyrrolidine,
3-chloro-3-ethylaminomethylpyrrolidine,
3-ethylaminomethyl-3-fluoropyrrolidine,
3-ethylaminomethyl-3-methylpyrrolidine,
3-ethylaminomethyl-3-mercaptopyrrolidine,
3-ethylaminomethyl-3-methylthiopyrrolidine,
3-acetoxy-3-ethylaminomethylpyrrolidine,
3-dimethylaminomethyl-3-hydroxypyrrolidine,
3-hydroxy-3-pyrrolidinomethylpyrrolidine,
3-hydroxy-3-morpholinomethylpyrrolidine,
3-amino-3-ethylaminomethylpyrrolidine,
3-acetylamino-3-ethylaminomethylpyrrolidine,
3-ethylaminomethyl-3-methylaminopyrrolidine,
3-dimethylamino-3-ethylaminomethylpyrrolidine,
3-amino-3-hydroxymethylpyrrolidine,
3-acetylamino-3-hydroxymethylpyrrolidine,
3-amino-3-methoxymethylpyrrolidine,
3-tert.-butoxycarbonylamino-3-methoxymethylpyrrolidine, 3-amino-3-methylthiomethylpyrrolidine,
3-amino-3-mercaptomethylpyrrolidine,
3-cyclopropylaminomethyl-3-hydroxypyrrolidine,
3-isopropylaminomethyl-3-hydroxypyrrolidine,
1,4-dioxa-7-azaspiro[4.4]nonane,
1-oxa-4,7-diazaspiro[4.4]nonane,
1-methyl-4-oxa-4,7-diazaspiro[4.4]nonane,
1-thia-4,7-diazaspiro[4.4]nonane,
1,4,7-triazaspiro[4.4]nonane,
1,4-dimethyl-1,4,7-triazaspiro[4.4]nonane.

The reaction of (II) with (III) is preferably performed in a diluent such as dimethyl sulphoxide, N,N-dimethylformamide, hexamethylphosphoric triamide, sulpholane, water, an alcohol such as methanol, ethanol, n-propanol, isopropanol, glycol monomethyl ether, acetonitrile or pyridine. Mixtures of these diluents can likewise be used.

All customary inorganic and organic acid-binding agents can be used as acid binders. These preferably include the alkali metal hydroxides, alkali metal carbonates, sodium hydride, organic amines and amidines. Those which may be mentioned individually as being particularly suitable are: triethylamine, 1,4-diazabicyclo[ 2,2,2]octane (DABCO), 1,8-diazabicyclo[5,4,0]undec-7-ene DBU) or excess amine (III).

The reaction temperatures can be varied within a relatively wide range. In general, the reaction is carried out between about 20° and 200° C., preferably between 80° and 180° C.

The reaction can be carried out at atmospheric pressure, but also at elevated pressure. In general, the reaction is carried out at pressures between about 1 and about 100 bar, preferably between 1 and 10 bar.

When carrying out the process according to the invention by method A, 1 to 15 moles, preferably 1 to 6 moles, of the amine (III) are employed per mole of carboxylic acid (II).

In addition to the compounds shown in the examples, the following may be mentioned individually as new active compounds:
9-fluoro-2,3-dihydro-10-(3-hydroxy-3-methylaminomethyl- 1-pyrrolidinyl)-3-methyl-7-oxo-7H-pyrido[1,2,3-de] [1,4] benzoxacine-6-carboxylic acid,
8-(3-ethylaminomethyl-3-hydroxy-1-pyrrolidinyl)-9-fluoro- 6,7-dihydro-5-methyl-1-oxo-1H,5H-benzo[i,j] quinolicine- 2-carboxylic acid,
and furthermore the compounds shown in the following table.

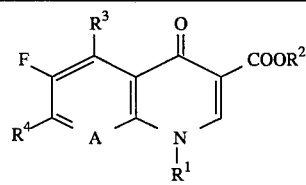

| Nr. | R¹ | R² | R³ | R⁴ | | A |
|---|---|---|---|---|---|---|
| 1 | cyclopropyl | H | H | CH₃—NHCH₂—C(OH)—(pyrrolidin-N—) | | CH |
| 2 | " | H | H | " | | N |
| 3 | " | H | H | " | | C—CH₃ |
| 4 | " | C₂H₅ | H | " | | CCl |
| 5 | " | —CH₂—C(=CH₃)—C(=O)—O—O (cyclic) | H | " | | CF |
| 6 | " | H | NH₂ | " | | CF |
| 7 | C₂H₅ | H | H | " | | CF |
| 8 | 2,4-difluorophenyl | H | H | CH₃—NHCH₂—C(OH)—(pyrrolidin-N—) | | CF |
| 9 | cyclopropyl | H | H | C₂H₅—NHCH₂—C(OH)—(pyrrolidin-N—) | | N |
| 10 | " | H | H | " | | C—CH₃ |
| 11 | " | H | NH₂ | " | | CF |

-continued

[Structure: quinolone core with R³ at 8-position, F at 6, R⁴ at 7, A at position between F and R⁴ ring junction; N-R¹ and COOR² with C=O]

| Nr. | R¹ | R² | R³ | R⁴ | A |
|---|---|---|---|---|---|
| 12 | C₂H₅ | H | H | " | CF |
| 13 | 4-F-C₆H₄ | H | H | " | N |
| 14 | cyclopropyl | C₂H₅ | H | " | CF |
| 15 | cyclopropyl | −CH₂−C(=C(CH₃)−O−)−O−C(=O)− (cyclic carbonate methylene) | H | C₂H₅−NHCH₂−C(OH)(−pyrrolidin-N−)− | CF |
| 16 | " | C₂H₅ | H | " | CCl |
| 17 | " | −CH₂−C(=C(CH₃)−O−)−O−C(=O)− | H | " | CCl |
| 18 | " | H | H | (CH₃)₂N−CH₂−C(OH)(−pyrrolidin-N−)− | CH |
| 19 | " | H | H | " | C−CH₃ |
| 20 | " | H | H | " | CCl |
| 21 | " | H | H | " | N |
| 22 | " | H | H | C₂H₅NH−CH₂−C(OCH₃)(−pyrrolidin-N−)− | CH |
| 23 | cyclopropyl | H | H | C₂H₅−NH−CH₂−C(OCH₃)(−pyrrolidin-N−)− | CF |
| 24 | " | H | H | " | CCl |
| 25 | " | H | H | C₂H₅−NH−CH₂−C(F)(−pyrrolidin-N−)− | CH |
| 26 | " | H | H | " | CF |
| 27 | " | H | H | " | CCl |
| 28 | " | H | H | " | N |

-continued

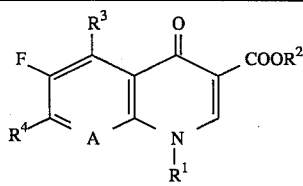

| Nr. | R¹ | R² | R³ | R⁴ | | A |
|---|---|---|---|---|---|---|
| 29 | " | H | H | $C_2H_5-NH-CH_2$, $CH_3S$ on quaternary C with pyrrolidine-N— | | CH |
| 30 | " | H | H | " | | CF |
| 31 | cyclopropyl | H | H | O, NH on quaternary C with pyrrolidine-N— | | CH |
| 32 | " | H | H | " | | CF |
| 33 | " | H | H | " | | CCl |
| 34 | " | H | H | " | | N |
| 35 | " | H | H | " | | $C-CH_3$ |
| 36 | " | H | H | $H_2N-CH_2$, HO on quaternary C with pyrrolidine-N— | | CF |
| 37 | " | H | H | " | | CCl |
| 38 | " | H | H | " | | N |
| 39 | " | H | H | $H_2N-CH_2$, HO on quaternary C with piperidine-N— | | CH |
| 40 | " | H | H | " | | CF |
| 41 | " | H | H | " | | CCl |
| 42 | cyclopropyl | H | H | $(CH_3)_2N-CH_2$, HO on quaternary C with piperidine-N— | | CH |
| 43 | " | H | H | " | | CF |

The compounds according to the invention show, combined with low toxicity, a broad antibacterial spectrum against gram-positive and gram-negative bacteria, in particular against Enterobacteriaceae; above all also against those which are resistant to various antibiotics, such as, for example, penicillins, cephalosporins, aminoglycosides, sulphonamides and tetracyclines.

These useful properties facilitate their use as chemotherapeutically active compounds in medicine and also as substances for the preservation of inorganic and organic materials, in particular of organic materials of all types, for example polymers, lubricants, dyes, fibers, leather, paper and wood, and of foodstuffs and water.

The compounds according to the invention are active against a very wide spectrum of microorganisms. Gram-negative and gram-positive bacteria and bacteria-like microorganisms can be controlled with their aid, and the diseases produced by these pathogens can also be prevented, improved and/or cured.

The compounds according to the invention are particularly active against bacteria and bacteria-like microorganisms. They are therefore particularly well suited in human and veterinary medicine for the prophylaxis and chemotherapy of local and systemic infections which are produced by these pathogens.

For example, local and/or systemic diseases which are caused by the following pathogens or by mixtures of the following pathogens can be treated and/or prevented: gram-positive cocci, for example staphylococci (*Staph. aureus, Staph. epidermidis*) and streptococci (*Strept. agalactiae, Strept. faecalis, Strept. pneumoniae, Strept. pyogenes*); gram-negative cocci (*Neisseria gonorrhoeae*) and also gram-negative rods such as Enterobacteriaceae, for example

*Escherichia coli, Haemophilus influenzae*, Citrobacter (*Citrob. freundii, Citrob. divernis*), Salmonella and Shigella; furthermore Klebsiella (*Klebs. pneumoniae, Klebs. oxytoca*), Enterobacter (*Ent. aerogenes, Ent. agglomerans*), Hafnia, Serratia (*Serr. marcescens*), Proteus (*Pt. mirabilis, Pt. rettgeri, Pr. vulgaris*), Providencia, Yersinia, and also the order Acinetobacter. Moreover, the antibacterial spectrum comprises the order Pseudomonas (*Ps. aeruginosa, Ps. maltophilia*) and also strictly anaerobic bacteria such as, for example, *Bacteroides fragilis*, representatives of the order Peptococcus, Peptostreptococcus and also the order Clostridium; furthermore mycoplasma (*M. pneumoniae, M. hominis, M. urealyticum*) and also mycobacteria, for example *Mycobacterium tuberculosis*.

The above enumeration of pathogens is merely by way of example and in no way to be conceived as limiting. Examples of diseases which may be caused by the said pathogens or mixed infections and which may be prevented, improved or cured by the compounds according to the invention which may be mentioned are:

infectious diseases in humans, such as, for example, otitis, pharyngitis, pneumonia, peritonitis, pyelonephritis, cystitis, endocarditis, systemic infections, bronchitis (acute, chronic), septic infections, diseases of the upper airways, diffuse panbronchiolitis, pulmonary emphysema, dysentery, enteritis, hepatic abscesses, urethritis, prostatitis, epididymitis, gastrointestinal infections, bone and joint infections, cystic fibrosis, skin infections, post-operative wound infections, abscesses, phlegmon, wound infections, infected burns, scalds, infections in the oral region, infections after dental operations, osteomyelitis, septic arthritis, cholecystitis, peritonitis with appendicitis, cholangitis, intra-abdominal abscesses, pancreatitis, sinusitis, mastoiditis, mastitis, tonsillitis, typhus, meningitis and infections of the nervous systems, salpingitis, endometritis, genital infections, pelveoperitonitis and eye infections.

In addition to humans, bacterial infections can also be treated in other species. Examples which may be mentioned are:

pig: coli-diarrhoea, enterotoxaemia, sepsis, dysentery, salmonellosis, mastitis-metritis-agalactia syndrome, mastitis;

ruminants (cow, sheep, goat): diarrhoea, sepsis, bronchopneumonia, salmonellosis, pasteurellosis, mycoplasmosis, genital infections;

horse: bronchopneumonias, joint-ill, puerperal and post-puerperal infections, salmonellosis;

dog and cat; bronchopneumonia, diarrhoea, dermatitis, otitis, urinary tract infections, prostatitis;

poultry (hen, turkey, quail, pigeon, ornamental birds and others): mycoplasmosis, *E. coli* infections, chronic airway diseases, salmonellosis, pasteurellosis, psittacosis.

Bacterial diseases in the rearing and keeping of productive and ornamental fish can likewise be treated, where the antibacterial spectrum is widened beyond the previously mentioned pathogens to further pathogens such as, for example, Pasteurella, Rucella, Campylobacter, Listeria, Erysipelothrix, Corynebacteria, Borrelia, Treponema, Nocardia, Rickettsia, Yersinia and Aeromonas, Edwardsiella and Vibria.

The present invention includes pharmaceutical preparations which contain one or more according to the invention or which consist of one or more active compounds according to the invention in addition to nontoxic, inert pharmaceutically suitable excipients and processes for the production of these preparations.

The present invention also includes pharmaceutical preparations in dosage units. This means that the preparations are in the form of individual portions, for example tablets, dragees, capsules, pills, suppositories and ampoules, whose active compound content corresponds to a fraction or a multiple of an individual dose. The dosage units may contain, for example, 1, 2, 3 or 4 individual doses or ½, ⅓ or ¼ of an individual dose. An individual dose preferably contains the amount of active compound which is administered in one application and which usually corresponds to a whole, a half, a third or a quarter of a daily dose.

Non-toxic, inert pharmaceutically suitable excipients are taken to mean solid, semi-solid or liquid diluents, fillers or formulation auxiliaries of any type.

Preferred pharmaceutical preparations which may be mentioned are tablets, dragees, capsules, pills, granules, suppositories, solutions, suspensions and emulsions, pastes, ointments, gels, creams, lotions, powders or sprays.

Tablets, dragees, capsules, pills and granules may contain the active compound(s) in addition to the customary excipients, such as (a) fillers and extenders, for example starches, lactose, sucrose, glucose, mannitol and silica, (b) binders, for example carboxymethylcellulose, alginates, gelatin, polyvinylpyrrolidone, (c) humectants, for example glycerol (d) disintegrants, for example agar—agar, calcium carbonate and sodium carbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i).

The tablets, dragees, capsules, pills and granules may be provided with the customary coatings and shells containing, if appropriate, opacifying agents and can be so composed that they release the active compound(s), if appropriate with a delay, only or preferably in a certain part of the intestinal tract, in which case, for example, polymeric substances and waxes can be used as embedding materials.

If appropriate, the active compound(s) may also be present in micro-encapsulated form with one or more of the abovementioned excipients.

In addition to the active compound(s) compound(s), suppositories may contain the customary water-soluble or water-insoluble excipients, for example polyethylene glycols, fats, for example cocoa fat and higher esters (for example $C_{14}$-alcohol with $C_{16}$-fatty acid) or mixtures of these substances.

Ointments, pastes, creams and gels may contain the customary excipients in addition to the active compound(s), for example animal and vegetable fats, waxes, paraffins, starch, tragacanth, cellulose derivatives, polyethylene glycols, silicones, bentonites, silica, talc and zinc oxide or mixtures of these substances.

Powders and sprays may contain the customary excipients in addition to the active compound(s), for example lactose, talc, silica, aluminum hydroxide, calcium silicate and polyamide powder or mixtures of these substances. Sprays may additionally contain the customary propellants, for example chlorofluorohydrocarbons.

Solutions and emulsions may contain the customary excipients, such as solvents, solubilizers and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polyethylene glycols and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example water, ethyl alcohol, propylene glycol, suspending agents, for example ethoxylated isostearyl alcohols, polyoxyethylene sorbitol and sorbitan esters, microcrystalline cellulose, aluminium metahydroxide, bentonite, agar—agar and tragacanth or mixtures of these substances in addition to the active compound(s).

The said formulation forms may also contain colorants, preservatives and also odour-improving and flavour-improving additives, for example peppermint oil and eucalyptus oil and sweeteners, for example saccharin.

The therapeutically active compounds should preferably be present in the abovementioned pharmaceutical preparations in a concentration of about 0.1 to 99.5, preferably of about 0.5 to 95% by weight, of the total mixture.

The abovementioned pharmaceutical preparations may also contain further pharmaceutical active compounds in addition to the compounds according to the invention.

The preparation of the abovementioned pharmaceutical preparations takes place in a customary manner by known methods, for example by mixing the active compound(s) with the excipient(s).

The preparations mentioned may be used in humans and animals either orally, rectally, parenterally (intravenously, intramuscularly, subcutaneously), intracisternally, intravaginally, intraperitoneally, locally (powders, ointments, drops) and for the therapy of infections in hollow spaces and body cavities. Suitable preparations are injection solutions, solutions and suspensions for oral therapy, gels, pour-on formulations, emulsions, ointments or drops. For local therapy, ophthalmological and dermatological formulations, silver salts and other salts, ear drops, eye ointments, powders or solutions may be used. In animals, the administration may also take place in suitable formulations via the feed or drinking water. Furthermore, gels, powders, tablets, delayed-release tablets, premixes, concentrates, granules, pellets, boli, capsules, aerosols, sprays and inhalants may be used in humans and animals. Furthermore, the compounds according to the invention may be incorporated into other excipients such as, for example, plastics, (plastic chains for local therapy), collagen or bone cement.

In general, it has proved advantageous both in human and veterinary medicine to administer the active compound(s) according to the invention in total amounts of about 0.5 to about 500, preferably 5 to 100 mg/kg of body weight every 24 hours, if appropriate in the form of several individual doses, to attain the desired results. An individual dose preferably contains the active compound(s) according to the invention in amounts of about 1 to about 80, in particular 3 to 30 mg/kg of body weight. However, it may be necessary to depart from the dosages mentioned, depending on the type and the body weight of the subject to be treated, the nature and severity of the disease, the type of preparation and the administration of the medicament and also the time period or interval within which the administration takes place.

Thus in some cases it may be sufficient to manage with less than the abovementioned amount of active compound, whereas in other cases the abovementioned amount of active compound must be exceeded. The optimum dosage required in each case and the type of administration of the active compounds can easily be established by anyone skilled in the art on the basis of his expert knowledge.

The new compounds may be given in the customary concentrations and preparations together with the feed or feed preparations or with the drinking water. Infection by gram-negative or gram-positive bacteria can thus be prevented, improved and/or cured and promotion of growth and an improvement in the utilization of the feed can thus be achieved.

The minimum inhibitory concentrations (MIC) were determined by the serial dilution method on iso-sensitest agar (Oxoid). A series of agar plates which contained concentrations of the active compound decreasing in double dilutions in each case were prepared for each test substance. The agar plates were inoculated using a multi-point inoculator (Denley). For the inoculation, overnight cultures of the pathogen were used which were previously diluted in such a way that each inoculation point contained about $10^4$ colony-forming particles. The inoculated agar plates were incubated at 37° C. and the bacterial growth was read off after about 20 hours. The MIC value (µg/ml) indicates the lowest active compound concentration with which no bacterial growth could be detected using the naked eye.

In the table below, the MIC values of some of the compounds according to the invention are indicated in comparison to ciprofloxacin and norfloxacin.

|  | Example | | | | | | | | ciprofloxacin | norfloxacin |
|---|---|---|---|---|---|---|---|---|---|---|
|  | 1 | 2 | 3 | 4 | 5 | 11 | 14 | 15 |  |  |
| *Staphylococcus aureus* | | | | | | | | | | |
| FK 422 | 0.5 | 0.125 | 0.5 | 0.062 | 0.25 | 0.062 | 0.125 | 0.031 | 0.25 | 0.5 |
| 1756 | 0.5 | 0.125 | 0.5 | 0.062 | 0.125 | 0.062 | 0.125 | 0.031 | 0.25 | 0.5 |
| 133 | 0.5 | 0.125 | 0.5 | 0.031 | 0.125 | 0.062 | 0.125 | 0.031 | 0.25 | 0.5 |
| *Streptococcus faecalis* (Enterococcus) | | | | | | | | | | |
| 27101 | 1 | 0.25 | 0.5 | 0.125 | 0.25 | 0.25 | 0.125 | 0.062 | 0.25 | 0.5 |
| 9790 | 1 | 0.25 | 0.5 | 0.125 | 0.25 | 0.25 | 0.125 | 0.062 | 0.25 | 0.5 |

Preparation Examples for intermediate compounds of the formula (III):

EXAMPLE A

3-Ethylaminomethyl-3-hydroxypyrrolidine a) Ethyl 5-aza-1-oxaspiro[2,4]heptane-5-carboxylate 23.5 g (107 mmol) of trimethylsulphoxonium iodide and 3.3 g of sodium hydride (80% strength in paraffin oil) are initially introduced and 80 ml of absolute dimethyl sulphoxide are added dropwise at 10° C. The mixture is stirred for an hour at room temperature and 15.7 g (100 mmol) of ethyl 3-oxopyrrolidine-1-carboxylate [J. Med. Pharm. Chem. 5, 752 (1962)] in 20 ml of absolute dimethyl sulphoxide are then added dropwise in the course of 15 minutes. The mixture is stirred for one hour at room temperature, poured onto a mixture of ice and saturated sodium chloride solution and extracted using diethyl ether. The ether solutions are washed with sodium chloride solution, dried over $Na_2SO_4$, concentrated and distilled.

Yield: 6 g

Boiling point: 80°C./0.15 mbar b) Ethyl 3-ethylaminomethyl-3-hydroxypyrrolidine-1-carboxylate 8 g (46.7 mmol) of ethyl 5-aza-1-oxaspiro[2,4] heptane-5-carboxylate are added dropwise to 50 ml of ethylamine solution (50% in water) and the mixture is stirred overnight at room temperature. It is concentrated and the residue is distilled.

Yield: 8 g

Boiling point: 130°C./0.05 mbar c) 3-Ethylaminomethyl-3-hydroxypyrrolidine 7.7 g (35.6 mmol) of ethyl 3-ethylaminomethyl-3-hydroxypyrrolidine-1-carboxylate are heated under reflux overnight with 22 g of $Ba(OH)_2 \cdot 8H_2O$ in 220 ml of water. The mixture is filtered off with suction from $BaCO_3$ and concentrated. The residue is boiled five times using 100 ml of dioxane each time, and the dioxane solution is concentrated and distilled.

Yield: 4.2 g

Boiling point: 70°–75° C./0.1 mbar

EXAMPLE B

3-Aminomethyl-3-hydroxypyrrolidine a) 3-Aminomethyl-1-benzyl-3-hydroxypyrrolidine 9.7 g (51.3 mmol) of 5-benzyl-5-aza-1-oxaspiro[2,4] heptane (U.S. Pat. No. 4,508,724) are added dropwise to 50 ml of ammonia solution (25%) and the mixture is stirred overnight at room temperature. The batch is then concentrated and the residue is distilled.

Yield: 4.4 g

Boiling point: 134° C./0.4 mbar b) 3-Aminomethyl-3-hydroxypyrrolidine 3.9 g (18.9 mmol) of 3-aminomethyl-1-benzyl-3-hydroxypyrrolidine in 25 ml of methanol are hydrogenated using 1 g of palladium/active carbon (10%) at 90° C. and 95 bar. The catalyst is filtered off, the filtrate is concentrated and the residue is distilled.

Yield: 1.2 g

Boiling point: 80° C./0.14 mbar

EXAMPLE C

3-Ethylaminomethyl-3-hydroxypyrrolidine a) 1-Benzyl-3-ethylaminomethyl-3-hydroxypyrrolidine 10.2 g (53.9 mmol) of 5-benzyl-5-aza-1-oxaspiro-[2,4] heptane are added dropwise to 60 ml of aqueous ethylamine solution (50%) and the mixture is stirred overnight at room temperature. The batch is then concentrated and the residue is distilled.

Yield: 10.7 g

Boiling point: 120° C./0.18 mbar b) 3-Ethylaminomethyl-3-hydroxypyrrolidine 10 g (42.7 mmol) of 1-benzyl-3-ethylaminomethyl-3-hydroxypyrrolidine in 60 ml of methanol are hydrogenated using 2 g of palladium/active carbon (10%) at 92°C. and 107 bar. The catalyst is filtered off, the filtrate is concentrated and the residue is distilled.

Yield: 4.8 g

Boiling point: 74° C./0.08 mbar

EXAMPLE D

3-Hydroxy-3-methylaminomethylpyrrolidine dihydrochloride a) 1-Benzyl-3-hydroxy-3-methylaminomethylpyrrolidine dihydrochloride 10.2 g (58.3 mmol) of 5-benzyl-5-aza-1-oxaspiro[2,4] heptane are added dropwise to 70 ml of aqueous methylamine solution (30%) and the mixture is stirred overnight at room temperature. The batch is then concentrated and the residue is distilled.

Yield: 8.8 g

Boiling point: 145° C./0.35 mbar

The distillate is dissolved in dilute hydrochloric acid and the solution is concentrated. The crystalline residue is triturated with isopropanol, filtered off with suction and dried.

Yield: 7.3 g

Melting point: 202° C.

b) 3-Hydroxy-3-methylaminomethylpyrrolidine dihydrochloride 6.9 g (23.5 mmol) of 1-benzyl-3-hydroxy-3-methylaminomethylpyrrolidine dihydrochloride in 100 ml of methanol are hydrogenated on 2 g of palladium/active carbon (10%) at 80°C. and 100 bar. The catalyst is filtered off with suction, the solution is concentrated and the residue is triturated with butanol. The crystalline salt is filtered off with suction, washed with acetone and dried.

Yield: 4 g

Melting point: 231°–232°C.

EXAMPLE E

3-Cyclopropylaminomethyl-3-hydroxypyrrolidine dihydrochloride a) 1-Benzyl-3-cyclopropylaminomethyl-3-hydroxypyrrolidine dihydrochloride 9.7 g (51.3 mmol) of 5-benzyl-5-aza-1-oxaspiro[ 2,4] heptane are added dropwise to 9.7 g (0.17 mol) of cyclopropylamine in 40 ml of water and the mixture is stirred overnight at room temperature. The batch is then concentrated and the residue is distilled.

Yield: 8 g

Boiling point: 130° C./0.08 mbar

The distillate is dissolved in dilute hydrochloric acid and the solution is concentrated. The residue which crystallizes is triturated with acetone, filtered off with suction and dried.

Yield: 8.3 g

Melting point: 182°–184° C.

b) 3-Cyclopropylaminomethyl-3-hydroxypyrrolidine dihydrochloride 7.9 g (24.7 mmol) of 1-benzyl-3-cyclopropylaminomethyl- 3-hydroxypyrrolidine dihydrochloride in 100 ml of methanol are hydrogenated on 2 g of palladium/active carbon (10%) at 50° C. and 100 bar. The product is filtered off with suction and concentrated, and the residue is triturated with butanol. The crystalline salt is filtered off with suction, washed with acetone and dried.

Yield: 3.4 g

EXAMPLE F

3-Aminomethyl-3-hydroxypiperidine a) Methyl 5-aza-1-oxaspiro[2,5]octane-5-carboxylate 23.5 g (107 mmol) of trimethylsulphoxonium iodide and 3.4 g (100 mmol) of NaH (80% in paraffin oil) are initially introduced and 80 ml of absolute dimethyl sulphoxide are added dropwise at 10° C. The mixture is stirred for one hour at room temperature and 15.8 g (100 mmol) of methyl 3-piperidone-1-carboxylate [Acta Chem. Scand. B 30, (1976), page 884] are then added dropwise in the course of 15 minutes. The mixture is stirred for one hour at room temperature, poured onto a mixture of ice and saturated sodium chloride solution and extracted using diethyl ether. The ether solution is washed with sodium chloride solution, dried over $Na_2SO_4$, concentrated and distilled.

Yield: 8 g

Boiling point: 68° C./0.15 mbar b) Methyl 3-aminomethyl-3-hydroxypiperidine-1-carboxylate 9.1 g (53.2 mmol) of methyl 5-aza-1-oxaspiro[ 2,5]octane-5-carboxylate are added dropwise to 50 ml of ammonia solution (25%) and the mixture is stirred overnight at room temperature. It is then concentrated and the residue is distilled.

Yield: 5.6 g

Boiling point: 103° C./0.1 mbar c) 3-Aminomethyl-3-hydroxypiperidine 5.1 g (27.1 mmol) of methyl 3-aminomethyl-3 -hydroxypiperidine-1-carboxylate are heated overnight under reflux with 15.8 g of $Ba(OH)_2 . 8H_2O$ in 150 ml water. The product is filtered off from $BaCO_3$ with suction and concentrated. The residue is boiled five times using 70 ml of dioxane each time, and the dioxane solutions are concentrated and distilled.

Yield: 1.8 g

Boiling point: 63° C./0.05 mbar

EXAMPLE G

3-Hydroxy-3-methylaminomethylpiperidine a) Methyl 3-hydroxy-3-methylaminomethylpiperidine-1-carboxylate 9.3 g (54.3 mmol) of methyl 5-aza-1-oxaspiro[ 2,5]octane-5-carboxylate are added dropwise to 50 ml of methylamine solution (25% in water) and the mixture is stirred overnight at room temperature. It is then concentrated and the residue is distilled.

Yield: 9.2 g

Boiling point: 83°–95°C./0.1 mbar b) 3-Hydroxy-3-methylaminomethylpiperidine 8.7 g (43 mmol) of methyl 3-hydroxy-3-methylaminomethylpiperidine- 1-carboxylate are heated overnight under reflux with 24 g of $Ba(OH)_2 . 8H_2O$ in 240 ml of water. The product is filtered off from $BaCO_3$ with suction and concentrated. The residue is boiled five times using 100 ml of dioxane each time, and the dioxane solution is concentrated and distilled.

Yield: 4.2 g

Boiling point: 56°C./0.05 mbar

EXAMPLE H

3-Ethylaminomethyl-3-hydroxypiperidine a) Methyl 3-ethylaminomethyl-3-hydroxypiperidine-1-carboxylate 9.3 g (54.3 mmol) of methyl 5-aza-1-oxaspiro[ 2,5]octane-5-carboxylate are added dropwise to 50 ml of ethylamine solution (50% strength in water) and the mixture is stirred overnight at room temperature. It is then concentrated and the residue is distilled.

Yield: 11.2 g

Boiling point: 104°–108° C./0.2 mbar b) 3-Ethylaminomethyl-3-hydroxypiperidine 10 g (46.2 mmol) of methyl 3-ethylaminomethyl-3 -hydroxypiperidine-1-carboxylate are heated under reflux overnight with 28.5 g of $Ba(OH)_2 . 8H_2O$ in 280 ml of water. The product is filtered off from $BaCO_3$ with suction and concentrated. The residue is boiled five times using 120 ml of dioxane each time, and the dioxane solution is concentrated and distilled.

Yield: 4.5 g

Boiling point: 70° C./0.09 mbar

EXAMPLE I

4-Aminomethyl-4-hydroxypiperidine dihydrochloride a) Ethyl 4-aminomethyl-4-hydroxypiperidine-1-carboxylate 13.4 g (72.3 mmol) of ethyl 6-aza-1-oxaspiro[2,5]octane-6-carboxylate (European Patent Application 189,370) are added dropwise to 60 ml of ammonia solution (25%) and the mixture is stirred overnight at room temperature. It is then concentrated and distilled.

Yield: 8.1 g

Boiling point: 110°–130°C./0.04 mbar b) 4-Aminomethyl-4-hydroxypiperidine dihydrochloride 1 g (4.9 mmol) of ethyl 4-aminomethyl-4-hydroxypiperidine-1-carboxylate is heated overnight under reflux with 10 ml of concentrated hydrochloric acid. The product is concentrated, and the crystals are triturated with acetone, filtered off with suction and dried in a vacuum desiccator over $P_4O_{10}$.

Yield: 1 g

Melting point: 230°–233° C.

EXAMPLE J

4-Hydroxy-4-methylaminomethylpiperidine dihydrochloride a) Ethyl 4-hydroxy-4-methylaminomethylpiperidine-1-carboxylate 5.2 g (28 mmol) of ethyl 6-aza-1-oxaspiro[2,5]-octane-6-carboxylate are added dropwise to 30 ml of methylamine solution (25% in water) and the mixture is stirred overnight at room temperature. It is then concentrated and recrystallized from petroleum ether (hygroscopic crystals).

Yield: 3.3 g b) 4-Hydroxy-4-methylaminomethylpiperidine dihydrochloride 3 g (13.9 mmol) of ethyl 4-hydroxy-4-methylaminomethylpiperidine-1-carboxylate are heated overnight under reflux with 30 ml of concentrated hydrochloric acid. The product is concentrated, and the crystals are stirred with acetone, filtered off with suction and dried in a vacuum desiccator over $P_4O_{10}$.

Yield: 2.7 g

Melting point: 236°–238° C.

EXAMPLE K

4-Dimethylaminomethyl-4-hydroxypiperidine dihydrochloride a) Ethyl 4-dimethylaminomethyl-4-hydroxypiperidine-1-carboxylate 5.2 g (28 mmol) of ethyl 6-aza-1-oxaspiro[2,5]octane-6-carboxylate are added dropwise to 30 ml of dimethylamine solution (40% in water) and the mixture is stirred overnight at room temperature. It is then concentrated and distilled.

Yield: 5.2 g

Boiling point: 150°–155°C./3 mbar b) 4-Dimethylaminomethyl-4-hydroxypiperidine dihydrochloride 4.5 g (19.4 mmol) of ethyl 4-dimethylaminomethyl-4-hydroxypiperidine-1-carboxylate are heated overnight under reflux with 35 ml of concentrated hydrochloric acid. The product is concentrated, and the crystals are triturated with acetone, filtered off with suction and dried in a vacuum desiccator over $P_4O_{10}$.

Yield: 4.1 g

Melting point: 224°–227° C.

EXAMPLE L

4-Ethylaminomethyl-4-hydroxypiperidine dihydrochloride a) Ethyl 4-ethylaminomethyl-4-hydroxypiperidine-1-carboxylate 5.7 g (30.8 mmol) of ethyl 6-aza-1-oxaspiro[2,5]octane-6-carboxylate are added dropwise to 30 ml of ethylamine solution (50% in water) and the mixture is stirred overnight at room temperature. It is then concentrated and distilled.

Yield: 5.5 g

Boiling point: 100°–104°C./0.01 mbar b) 4-Ethylaminomethyl-4-hydroxypiperidine dihydrochloride 4.6 g (20 mmol) of ethyl 4-ethylaminomethyl-4-hydroxypiperidine-1-carboxylate are heated overnight under reflux with 35 ml of concentrated hydrochloric acid. The product is concentrated, and the crystals are triturated with acetone, filtered off with suction and dried in a vacuum desiccator over $P_4O_{10}$.

Yield: 4.2 g

Melting point: 225°–229° C.

EXAMPLE M

3-Hydroxy-3-methylpyrrolidine 15 g (78.4 mmol) of 1-benzyl-3-hydroxy-3-methylpyrrolidine (European Patent Application 132,845) are dissolved in 150 ml of ethanol and hydrogenated on 2 g of palladium/active carbon (10% Pd) at 90°C. and 100 bar. The catalyst is subsequently filtered off with suction, the filtrate is concentrated and the residue is distilled.

Yield: 4.6 g

Boiling point: 60°–64°C./0.08 mbar

EXAMPLE N

3-Dimethylaminomethyl-3-hydroxypyrrolidine a) 1-Benzyl-3-dimethylaminomethyl-3-hydroxypyrrolidine 9.6 g (50 mmol) of 5-benzyl-5-aza-1-oxaspiro[2,4]heptane are added dropwise to 50 ml of dimethylamine solution (50%) and the mixture is stirred overnight at room temperature. The batch is then concentrated and the residue is distilled.

Yield: 10.3 g

Boiling point: 94° C./0.05 mbar b) 3-Dimethylaminomethyl-3-hydroxypyrrolidine 9.4 g (39 mmol) of 1-benzyl-3-dimethylaminomethyl-3-hydroxypyrrolidine in 60 ml of methanol are hydrogenated using 2 g of palladium/active carbon (5%) at 100°C. and 90 bar. The catalyst is filtered off, the filtrate is concentrated and the residue is distilled.

Yield: 4.3 g
Boiling point: 51° C./0.06 mbar.

EXAMPLE O

3-Hydroxy-3-methoxymethylpyrrolidine a) 1-Benzyl-3-hydroxy-3-methoxymethylpyrrolidine 26.8 g (0.14 mol) of 5-benzyl-1-oxa-5-azaspiro[ 2,4] heptane are heated overnight under reflux with 2.6 ml (14 mmol) of 30% strength sodium methoxide solution in 200 ml of absolute methanol. The product is concentrated and distilled.

Yield: 25.6g (83% of theory)
Boiling point: 107°–112° C./0.15 mbar b) 3-Hydroxy-3-methoxymethylpyrrolidine 10 g (45 mmol) of 1-benzyl-3-hydroxy-3-methoxymethylpyrrolidine are hydrogenated using 3 g of Pd/active carbon (10% Pd) in 200 ml of methanol at 100° C. and 100 bar. The catalyst is filtered off with suction, the filtrate is concentrated and the residue is distilled.

Yield: 4.7 g (80% of theory)
Boiling point: 65° C./0.4 mbar

EXAMPLE P 3-tert.-Butoxycarbonylaminomethyl-3-hydroxypyrrolidine a) 1-Benzyl-3-tert.-butoxycarbonylaminomethyl-3-hydroxypyrrolidine 3.2 g (80 mmol) of NaOH are dissolved in 40 ml of water, 15.6 g (75 mmol) of 3-aminomethyl-1-benzyl-3-hydroxypyrrolidine and 50 ml of tert.-butanol are added and 17.7 g (79 mmol) of di-tert.-butyl dicarbonate are added dropwise at room temperature. After stirring overnight at room temperature, the product is filtered off with suction, the crystals are washed with $CH_2Cl_2$ and the filtrate is extracted using $CH_2Cl_2$. The extracts are dried over $K_2CO_3$ and concentrated, and the residue is recrystallized from diisopropyl ether.

Yield: 19.1 g (83% of theory)
Melting point: 117°–119° C.

b) 3-tert.-Butoxycarbonylaminomethyl-3-hydroxypyrrolidine 18.7 g (61 mmol) of 1-benzyl-3-tert.-butoxycarbonylaminomethyl- 3-hydroxypyrrolidine are dissolved in 120 ml of methanol and hydrogenated on 3 g of 5% strength Pd/active carbon at 90° C. and 100 bar. The catalyst is filtered off, the filtrate is concentrated and the residue is recrystallized from ethyl acetate.

Yield: 9.2 g (70% of theory)
Melting point: 124°–127°C.

EXAMPLE Q

3-Methoxy-3-methylaminomethylpyrrolidine a) 1-Benzyl-3-benzylmethylaminomethyl-3-hydroxypyrrolidine 18.2 g (95 mmol) of 5-benzyl-1-oxa-5-azaspiro[2,4]heptane are added dropwise to 15.6 ml (0.115 mol) of benzylmethylamine in 300 ml of water and the mixture is stirred for 15 hours at room temperature. The product is extracted using $CH_2Cl_2$, the extracts are dried using $K_2CO_3$ and concentrated, and incipient distillation is carried out up to 160° C. (oil bath temperature).

Crude yield: 27.1 g
GC purity: 100% b) 1-Benzyl-3-benzylmethylaminomethyl-3-methoxypyrrolidine 26 g (83 mmol) of crude 1-benzyl-3-benzylmethylaminomethyl- 3-hydroxypyrrolidine in 50 ml of absolute tetrahydrofuran are added dropwise to 4 g of 80% strength sodium hydride in 100 ml of absolute tetrahydrofuran and the mixture is heated under reflux during this. After completion of hydrogen evolution, 12.4 g (87 mmol) of methyl iodide are slowly added dropwise and the mixture is subsequently heated overnight under reflux. The product is poured into ice water and extracted using toluene, the extract is dried over $K_2CO_3$ and concentrated, and the residue is distilled.

Yield: 16.5 g
Boiling range: 140°–173° C./0.1–0.23 mbar
After repeated distillation:
Yield: 9.1 g (26% of theory)
GC purity: 80%
Boiling point: 141°C./0.07 mbar c) 3-Methoxy-3-methylaminomethylpyrrolidine 8.4 g (20 mmol) of 80% strength 1-benzyl-3-benzylmethylaminomethyl- 3-methoxypyrrolidine are dissolved in 100 of methanol, 4.4 ml of concentrated hydrochloric acid are added and the mixture is hydrogenated on 4 g of 10% strength Pd/active carbon at 80° C. and 120 bar. The catalyst is filtered off, the solution is concentrated, a solution of 3 g of KOH in 50 ml of methanol are added, KCl is filtered off and the solution is concentrated. The residue is taken up in $CHCl_3$ again, the mixture is filtered, the solution is concentrated and the residue is distilled.

Yield: 1.7 g (59% of theory)
Boiling point: 33°C./0.08 mbar

Additional examples concerning intermediates following the examples A to Q, pages 31 to 42

EXAMPLE R

3-Isopropylaminomethyl-3-hydroxy-pyrrolidine a)
1-Benzyl-isopropylaminomethyl-3-hydroxy-pyrrolidine

To a mixture of 20.65 g (0,35 mol) isopropylamine and 75 ml water 18.9 g (0,1 mol) 5-benzyl-1-oxa-5-azaspiro[2.4] heptane are added dropwise and the mixture is stirred for 15 hours at room temperature. The mixture is extracted with chloroform, and the organic layer is separated, dried with potassiumcarbonate and finally the solvent is removed in vacuo.

Yield: 22.3 g (90% of theory)
Boiling point: 111° C./0, 1 mbar.

b) 3-Isopropylaminomethyl-3-hydroxy-pyrrolidine 17.4 g (70 mmol) 1-Benzyl-isopropylaminomethyl-3-hydroxy-pyrrolidine are dissolved in 200 ml of ethanol. This solution is hydrogenated, using 10 g Pd-C (10%) at 100 bar/100° C. The catalyst is removed by filtration, the solvents are removed from the filtrate in vacuo.

Yield: 7.3 g (66% of theory)

Analogously to example R the compounds of the following examples are obtained from the respective amines:

EXAMPLE S

3-Diethylaminomethyl-3-hydroxy-pyrrolidine a)
1-Benzyl-3-diethylaminomethyl-3hydroxy-pyrrolidine Yield: 85% of theory
Boiling point: 120° C./0.01 mbar.

b) 3-Diethylaminomethyl-3-hydroxy-pyrrolidine

Yield: 72% of theory
Boiling point: 90° C./0.05 mbar.

EXAMPLE T a)
1-Benzyl-3-hydroxy-3-(1-pyrrolidinyl)-pyrrolidine

Yield: 79% of theory
Boiling point: 132° C./0.07 mbar.

b) 3-Hydroxy-3-(1-pyrrolidinyl)-pyrrolidine

EXAMPLE U

3-Hydroxy-3-(4-mopholinyl)-pyrrolidine a)
1-Benzyl-3-hydroxy-3-(4-morpholinyl)-pyrrolidine Yield: 88% of theory
Boiling point: 154° C./0.4 mbar.

b) 3-Hydroxy-3-(4-morpholinyl)-pyrrolidine

Yield: 60% of theory
Boiling point: 104° C./0.2 mbar.

EXAMPLE V 3-(N-ethyl-N-methyl-aminomethyl)-3-hydroxy-pyrrolidine a) 1-Benzyl-3-(N-ethyl-N-methyl-aminomethyl)-3-hydroxy-pyrrolidine Yield: 76% of theory
Boiling point: 110° C./0.08 mbar.

b) 3-(N-ethyl-N-methyl-aminomethyl)-3-hydroxy-pyrrolidine

Yield: 67% of theory
Boiling point: 70° C./0.08 mbar.

c) An alternative synthesis für 1-benzyl-3-(N-ethyl-N-methyl-aminomethyl)-3-hydroxy-pyrrolidine is as follows:

1.8 g (93 mmol) 1-benzyl-3-ethylaminomethyl-3-hydroxy-pyrrolidine (according to example Ca) are dissolved in a mixture of 9.5 g formic acid and 8.5 g 37% proof aqueous formaldehyde solution. The mixture is stirred at 80° C. for 4 hours. The solvents are removed in vacuo, the residue is taken up in water, and the pH is adjusted alkaline with potassium carbonate. The reaction mixture is then extracted with chloroforme, and the organic phase is dried with potassium carbonate. After filtration the organic solvent is removed in vacuo and the residue is destilled.

Yield: 17.8 g (85% of theory)
Boiling point: 110° C./0.08 mbar.

EXAMPLE W a) 1-Benzyl-3-cyano-3-methoxy-pyrrolidine

To a mixture of 1.2 g triflouroacetic acid and 1.2 g triethylamine in 200 ml dry dichloromethane 8.3 g (90 mmol, 90% proof) 2-methoxyacrylonitrile (J. Chem. Soc. 520, 1942) are added. Thereafter 28.5 g N-benzyl-N-methoxymethyl-N-(trimethylsilylmethyl)-amine (Chem. Letters 1117, 1984) are added, and the mixture is stirred overnight at room temperature. The mixture is treated with a saturated solution of sodium hydrogencarbonate, dried with magnesiumsulfate, and finally the organic solvents are removed in vacuo and the residue is destilled.

Yield: 14 g (67% of theory)
Boiling point: 110° C./0.2 mbar
Purity: 93% proof (gas chromatography).

b) 3-Aminomethyl-1-bezyl-3-methoxy-pyrrolidine

The solution of 26.5 g (0.11 mol, 93% proof) 1-benzyl-3-cyano-3-methoxypyrrolidine in 300 ml methanole is hydrogenated at 15 g Raney-Ni at 60° C./100 bar $H_2$. The catalyst is removed by filtration, the methanol is removed in vacuo, and the residue is destilled.

Yield: 15.6 g (64% of theory)
Boiling Point: 107°–110° C./0.15 mbar.

c)
1-Benzyl-3-(tert.-butoxycarbonylamino-methyl)-3-methoxy-pyrrolidine

To a mixture of 19.5 g (88.5 mmol) 3-amino-methyl-1-benzyl-3-methoxy-pyrrolidine and 100 ml tert.-butanole 3.7 g sodium hydroxyde in 90 ml water are added. Thereafter 20 g pyro-carbonic acid-tert.-butylester is added dropwise. The mixture is stirred overnight at room temperature, and the precipitates are removed by filtration. The filtrate is extracted with chloroform, and the organic layer is separated and dried with magnesiumsulfate. The organic solvents are removed in vacuo, and the residue is destilled.

Yield: 26 g (91.7% of theory)
Boiling point: 155°–160° C./0.02 mbar.

d) 3-(tert.-Butoxycarbonylamino-methyl)-3-methoxy-pyrrolidine 12 g (37.4 mmol) 1-benzyl-3-(tert.-butoxy-carbonylamino-methyl)-3-methoxypyrrolidine is desolved in 150 ml ethanol. This solution is hydrogeneted at 4 g Pd-carbon (10 %) at 100° C./100 bar $H_2$. The catalyst is removed by filtration, and the organic solvents are removed in vacuo. The residue is destilled.

Yield: 6.3 g (72.9% of theory)
Boiling point: 108°–111° C./0.2 mbar.

EXAMPLE X a) 1-Benzyl-3-(tert.-butylaminomethyl)-3-hydroxy-pyrrolidine

A 0.1 molar run according to example R a) yielded 21.6 g (81.5% of theory), boiling point: 120° C./0.07 mbar.

b) 3-(tert.-Butylaminomethyl)-3-hydroxy-pyrrolidine

A 82.3 mmolar run according to example R b) yielded 9.6 g (65.5% of theory), boiling point: 109° C./0.06 mbar.

EXAMPLE Y a) 3-Azetidinylmethyl-3-hydroxypyrrolidine-1-carboxylic acid-ethylester

A 21 mmolar run with 1.5 g (26 mmol) azetidine according to example A b) yielded 4.3 g (85.2% of theory), boiling point: 112°–113° C./0.02 mbar. The compound is 95% proof (gas chromatography).

b) 3-Azetidinylmethynyl-3-hydroxy-pyrrolidine

A 16 mmolar run according to example A c) yielded 1.4 g (56% of theory), boiling point: 95° C./0.35 mbar.

EXAMPLE Z a) 1-Benzyl-3-methoxypyrrolidine-3-carboxylic acid metyhlester

A 0.75 molar run according to example W a), using 2-methoxy-acrylic acid-methylester (Bull. Chem. Soc. Jpn 43, 2987 (1970)) yielded: 78.2 g (41,6% of theory), boiling point: 130°–134° C./0.04 mbar (after redestillation). The product is 94% proof (gas chromatography).

b) 1-Benzyl-3-hydroxymethyl-3-methoxypyrrolidine 6.5 g Lithium aluminum hydride are suspended in 250 ml of dry diethylether. 42 g (0.16 mol) 1-benzyl-3-methoxy-pyrrolidine-3-carboxylic acidmethylester are added dropwise. The mixture is stirred for 2 hours under reflux. Thereafter 6.5 ml of water, 6.5 ml 15% proof KOH and 6.5 ml of water are added, the inorganic salts are removed by filtration and washed twice with tetrahydrofurane. The organic solvents are removed from the filtrate in vacuo and the resedue is destilled.

Yield: 28.8 g (82% of theory)
Boiling point: 116°–120° C./0.03 mbar.

c) 3-Hydroxymethyl-3-methoxypyrrolidine

A 24.8 mmolar run according to example W d) yielded 1.2 g (36.9 % of theory), boiling point 76° C./0.07 mbar.

EXAMPLE 1

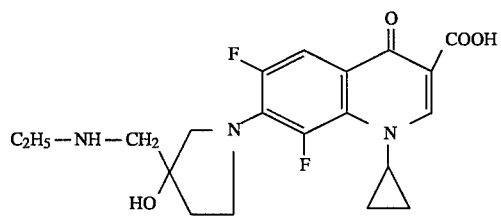

A mixture of 1.4 g (5 mmol) of 1-cyclopropyl- 6,7,8-trifluoro-1,4-dihydro-4-oxo-3-quinolinecarboxylic acid, 1.1 g (10 mmol) of 1,4-diazabicyclo[2.2.2]octane and 0.8 g (5.5 mmol) of 3-ethylaminomethyl-3-hydroxypyrrolidine in 10 ml of acetonitrile and 5 ml of dimethylformamide is heated under reflux for 1 hour. The suspension is concentrated in vacuo, the residue is stirred well with water, and the remaining precipitate is filtered off with suction, washed with water, dried and recrystallized from glycol monomethyl ether. Yield: 1.2 g (59% of theory) of 1-cyclopropyl-7-(3-ethylaminomethyl- 3-hydroxy-1-pyrrolidinyl)-6,8-difluoro-1,4 -dihydro-4-oxo-3-quinolinecarboxylic acid of melting point 230°–232° (with decomposition).

EXAMPLE 2

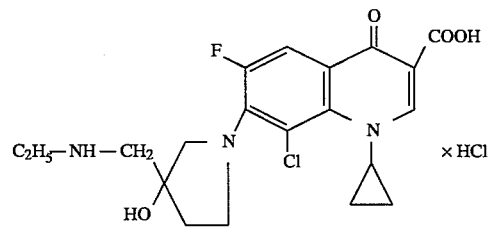

1.1 g (10 mmol) of 1,4-diazabicyclo[2.2.2]octane and 0.8 g (5.5 mmol) of 3-ethylaminomethyl-3-hydroxypyrrolidine are added to 1.5 g (5 mmol) of 8-chloro-1-cyclopropyl-6,7-difluoro-1,4-dihydro-4-oxo-3-quinolinecarboxylic acid in 10 ml of acetonitrile and 5 ml of dimethylformamide and the mixture is heated under reflux for 1 hour. The suspension is concentrated, and the residue is filtered off with suction, washed with water and brought into solution with a little 1:1 hydrochloric acid. The hydrochloride is precipitated by the addition of ethanol. It is filtered off with suction, washed with ethanol and dried at 100° in vacuo.

Yield: 1.3 g (56.5% of theory) of 8-chloro-1-cyclopropyl-7-(3-ethylaminomethyl-3-hydroxy-1-pyrrolidinyl)-6-fluoro-1,4-dihydro-4-oxo-3-quinolinecarboxylic acid hydrochloride of melting point 222°–223° (with decomposition).

EXAMPLE 3

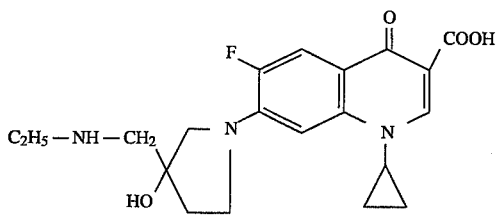

1-Cyclopropyl-6,7-difluoro-1,4-dihydro-4-oxo-3-quinolinecarboxylic acid is reacted analogously to Example 1 to give 1-cyclopropyl-7-(3-ethylaminomethyl-3 -hydroxy-1-pyrrolidinyl)-6-fluoro-1,4-dihydro-4-oxo-3 -quinolinecarboxylic acid of melting point 202°–207°.

EXAMPLE 4

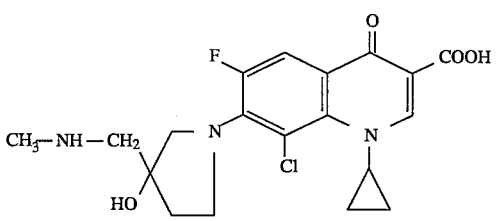

1.5 g (5 mmol) of 8-chloro-1-cyclopropyl-6,7-difluoro-1, 4-dihydro-4-oxo-3-quinolinecarboxylic acid are heated under reflux for 1 hour with 2.2 g (20 mmol) of 1,4-diazabicyclo[2.2.2]octane and 1.12 g (5.5 mmol) of 3-hydroxy-3-methylaminomethylpyrrolidine dihydrochloride in 10 ml of acetonitrile and 5 ml of dimethylformamide. The suspension is concentrated, the residue is stirred with water and the undissolved product is filtered off with suction, washed with water and dried. The crude product obtained (1.97 g) is recrystallized from dimethylformamide.

Yield: 1.55 g (75.7% of theory) of 8-chloro-1-cyclopropyl- 6-fluoro-1,4-dihydro-7-(3-hydroxy-3-methylaminomethyl- 1-pyrrolidinyl)-4-oxo-3-quinolinecarboxylic acid of melting point 266°–268° (with decomposition).

EXAMPLE 5

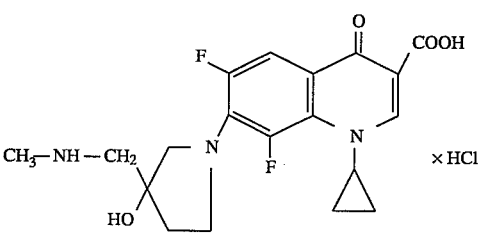

1-Cyclopropyl-6,7,8-trifluoro-1,4-dihydro-4-oxo-3-quinolinecarboxylic acid is reacted analogously to Example 4, the crude product obtained (1.75 g) is dissolved in 10 ml of 1:1 hydrochloric acid, and the hydrochloride is precipitated by adding ethanol, filtered off with suction, washed with ethanol and dried at 100° in vacuo.

Yield: 1.2 g (56% of theory) of 1-cyclopropyl-6,8-difluoro- 1,4-dihydro-7-(3-hydroxy-3-methylaminomethyl-1 -pyrrolidinyl)-4-oxo-3-quinolinecarboxylic acid hydrochloride of melting point 274°–276° (with decomposition).

EXAMPLE 6

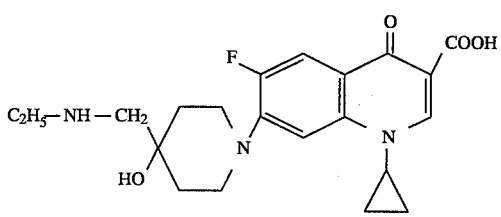

3.3 g (30 mmol) of 1,4-diazabicyclo[2.2.2]octane and 2.5 g (11 mmol) of 4-ethylaminomethyl-4-hydroxypiperidine dihydrochloride are added to 2.65 g (10 mmol) of 1-cyclopropyl-6,7-difluoro-1,4-dihydro-4-oxo-3-quinolinecarboxylic acid in a mixture of 20 ml of acetonitrile and 10 ml of dimethylformamide and the mixture is heated under reflux for 1 hour. The suspension is concentrated, the residue is stirred with water (pH 7), and the precipitate is filtered off with suction, washed with water, dried and recrystallized from dimethylformamide.

Yield: 3.03 g (75.2% of theory) of 1-cyclopropyl-7-(4 -ethylaminomethyl-4-hydroxy-1-piperidinyl)-6-fluoro-1,4-dihydro-4-oxo-3-quinolinecarboxylic acid of melting point 258°–259° (with decomposition).

EXAMPLE 7

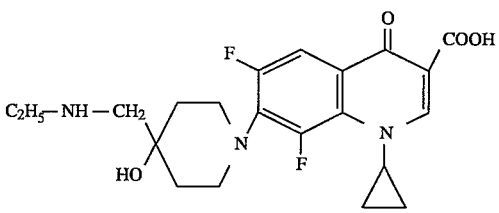

1-Cyclopropyl-6,7,8-trifluoro-1,4-dihydro-4-oxo-3-quinolinecarboxylic acid is employed analogously to Example 6 and 1-cyclopropyl-7-(4-ethylaminomethyl-4 -hydroxy-1-piperidinyl)-6,8-difluoro-1,4-dihydro-4-oxo-3-quinolinecarboxylic acid of melting point 270°–280° (with decomposition) are obtained.

EXAMPLE 8

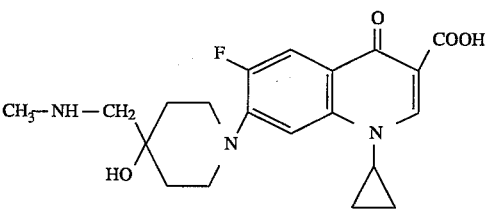

1-Cyclopropyl-6,7-difluoro-1,4-dihydro-4-oxo-3-quinolinecarboxylic acid is reacted with 4-hydroxy-4-methylaminomethylpiperidine dihydrochloride analogously to Example 6 to give 1-cyclopropyl-6-fluoro-1,4-dihydro-7-(4-hydroxy-4-methylaminomethyl-1-piperidinyl)-4-oxo-3-quinolinecarboxylic acid of melting point 162° (with decomposition).

EXAMPLE 9

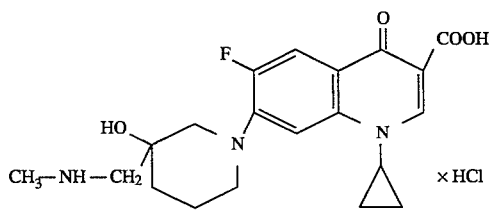

1-Cyclopropyl-6,7-difluoro-1,4-dihydro-4-oxo-3-quinolinecarboxylic acid is reacted analogously to Example 2 with 3-hydroxy-3-methylaminomethylpiperidine to give 1-cyclopropyl-6-fluoro-1,4-dihydro-7-(3-hydroxy- 3-methylaminomethyl-1-piperidinyl)-4-oxo-3-quinolinecarboxylic acid hydrochloride of melting point 293°–296° (with decomposition).

EXAMPLE 10

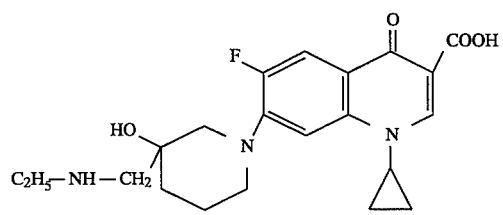

1-Cyclopropyl-6,7-difluoro-1,4-dihydro-4-oxo-3-quinolinecarboxylic acid is reacted analogously to Example 1 with 3-ethylaminomethyl-3-hydroxypiperidine to give 1-cyclopropyl-7-(3-ethylaminomethyl-3-hydroxy-1-piperidinyl)-6-fluoro-1,4-dihydro-4-oxo-3-quinolinecarboxylic acid of melting point 199°–203°C. (with decomposition).

EXAMPLE 11

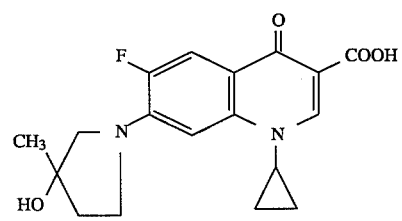

1.3 g (5 mmol) of 1-cyclopropyl-6,7-difluoro-1,4-dihydro-4-oxo-3-quinolinecarboxylic acid are heated under reflux for 1 hour with 1.1 g (10 mmol) of 1,4-diazabicyclo[2.2.2]octane and 540 mg (5.4 mmol) of 3-hydroxy-3-methylpyrrolidine in 10 ml of acetonitrile and 5 ml of dimethylformamide. The suspension is concentrated; the residue is stirred with water, and the precipitate is filtered off with suction, washed with water, recrystallized from dimethylformamide and dried at 100° in vacuo.

Yield: 1.4 g (81% of theory) of 1-cyclopropyl-6-fluoro-1,4-dihydro-7-(3-hydroxy-3-methyl-1-pyrrolidinyl)-4-oxo-3-quinolinecarboxylic acid of melting point 315°–320° (with decomposition).

EXAMPLE 12

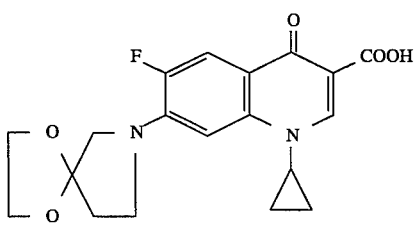

1-Cyclopropyl-6,7-difluoro-1,4-dihydro-4-oxo-3 -quinolinecarboxylic acid is reacted analogously to Example 11 with 1,4-dioxa-7-azaspiro[4.4]nonane to give 1-cyclopropyl-7-(1,4-dioxa-7-azaspiro[4.4]non-7-yl)-6-fluoro-1,4-dihydro-4-oxo-3-quinolinecarboxylic acid of melting point 229°–230°.

EXAMPLE 13

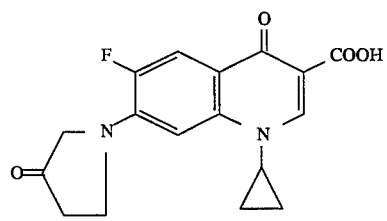

2 g of 1-cyclopropyl-7-(1,4-dioxa-7-azaspiro[4.4]non-7-yl)-6-fluoro-1,4-dihydro-4-oxo-3-quinolinecarboxylic acid are suspended in 100 ml of methanol and stirred for 2 hours at room temperature with 100 ml of 1:1 hydrochloric acid. The suspension is concentrated and the residue is recrystallized from dimethylformamide.

Yield: 1 g (52% of theory) of 1-cyclopropyl-6-fluoro-1,4-dihydro-4-oxo-7-(3-oxo-1-pyrrolidinyl)-3-quinolinecarboxylic acid of melting point 286°–288° (with decomposition).

EXAMPLE 14

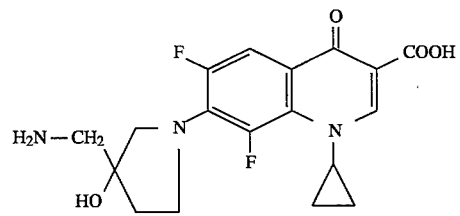

3-Aminomethyl-3-hydroxypyrrolidine is reacted according to Example 1 to give 7-(3-aminomethyl-3-hydroxy-1-pyrrolidinyl)-1-cyclopropyl-6,8-difluoro-1,4 -dihydro-4-oxo-3-quinolinecarboxylic acid of melting point 248° C. (with decomposition).

Mass spectrum: m/e 379 ($M^{30}$), 361 (379-$H_2O$), 344 (361-F), 44 ($CO_2$), 41 ($C_3H_5$), 18 ($H_2O$).

EXAMPLE 15

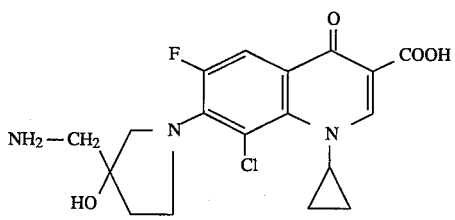

8-Chloro-1-cyclopropyl-6,7-difluoro-1,4-dihydro- 4-oxo-3-quinolinecarboxylic acid is reacted analogously to Example 14, the product obtained is purified by chromatography on silica gel using dichloromethane/methanol/20% aqueous ammonia solution (2:4:1) as eluant and 7-(3-aminomethyl-3-hydroxy-1-pyrrolidinyl)-8-chloro- 1-cyclopropyl-6-fluoro-1,4-dihydro-4-oxo-3-quinolinecarboxylic acid of melting point 240°–243° C. (with decomposition) are obtained.

FAB mass spectrum: m/e 396 [(M+H$^+$)], 368 [(M+H–CO$^+$)]

EXAMPLE 16

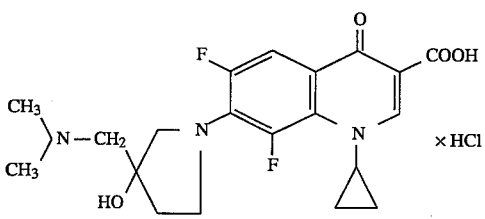

1.42 g (5 mmol) of 1-cyclopropyl-6,7,8-trifluoro- 1,4-dihydro-4-oxo-3-quinolinecarboxylic acid are heated under reflux for 1 hour in a mixture of 10 ml of acetonitrile and 5 ml of dimethylformamide and 0.8 g (5.6 mmol) of 3-hydroxy-3-dimethylaminomethyl-pyrrolidine and 1.1 g (10 mmol) of 1,4-diazabicyclo[2.2.2]octane. The suspension is concentrated, water is added to the residue and the mixture is acidified with dilute hydrochloric acid (1:1), The salt which crystallizes out is filtered off with suction and recrystallized from dimethylformamide.

Yield: 1.1 g (50% of theory) of 1-cyclopropyl-6,8-difluoro- 1,4-dihydro-7-(3-hydroxy-3-dimethylaminomethyl-1-pyrrolidinyl)-4-oxo-3-quinolinecarboxylic acid hydrochloride of melting point 292°–295° C. (with decomposition).

EXAMPLE 17

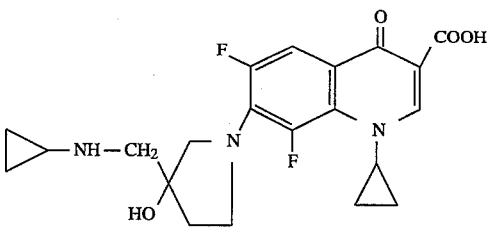

1-Cyclopropyl-6,7,8-trifluoro-1,4-dihydro-4-oxo-3-quinolinecarboxylic acid is reacted analogously to Example 6 with 3-cyclopropylaminomethyl-3-hydroxypyrrolidine dihydrochloride to give 1-cyclopropyl-7-(3-cyclopropylaminomethyl- 3-hydroxy-1-pyrrolidinyl)-6,8-difluoro- 1,4-dihydro-4-oxo-3-quinolinecarboxylic acid of melting point 161°– 162° (with decomposition).

EXAMPLE 18

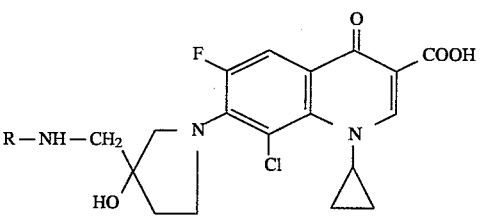

a) R = (CH$_3$)$_3$C—O—CO
b) R = H x HCl a) A mixture of 6 g (20 mmol) of 8-chloro-1-cyclopropyl-6,7-difluoro-1,4-dihydro-4-oxo-3-quinolinecarboxylic A 25 727 acid, 2.5 g (22.7 mmol) of 1,4-diazabicyclo[ 2.2.2] octane and 4.2 g (20 mmol) of 3-tert.-butoxycarbonylaminomethyl- 3-hydroxypyrrolidine in 40 ml of acetonitrile and 20 ml of dimethylformamide is heated under reflux for 3 hours. The solution is concentrated in vacuo, the residue is stirred with water, and the undissolved precipitate is filtered off with suction, washed with water and dried.

Yield: 9.8 g (99% of theory) of crude 7-(3-tert.-butoxycarbonylaminomethyl- 3-hydroxy-1-pyrrolidinyl)-8-chloro- 1-cyclopropyl-6-fluoro-1,4-dihydro-4-oxo-3-quinolinecarboxylic acid.

Melting point: 192° C. (with decomposition) (after recrystallization from ethanol).

b) 9.5 g (19 mmol) of the product from Example 18a) are stirred for 30 minutes at room temperature in 300 ml of 1:1 hydrochloric acid. The mixture is filtered and the filtrate is concentrated at 35° C./12 mbar. The residue is recrystallized from glycol monomethyl ether.

Yield: 4.3 g (52% of theory) of 7-(3-aminomethyl-3 -hydroxy-1-pyrrolidinyl)-8-chloro-1-cyclopropyl-6-fluoro-1,4-dihydro-4-oxo-3-quinolinecarboxylic acid hydrochloride of melting point 147°–150° C. (with decomposition);

Purity: 93% pure (by HPLC).

EXAMPLE 19

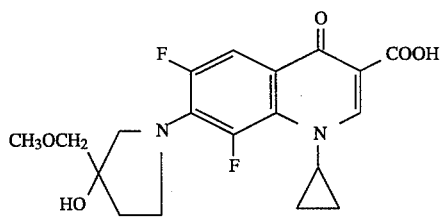

3-Hydroxy-3-methoxymethylpyrrolidine is reacted analogously to Example 1 and 1-cyclopropyl-6,8-difluoro- 1,4-dihydro-7-(3-hydroxy-3-methoxymethyl-1-pyrrolidinyl)-4-oxo-3-quinolinecarboxylic acid of melting point 230°–232° (with decomposition) (recrystallized from dimethylformamide) is obtained.

EXAMPLE 20

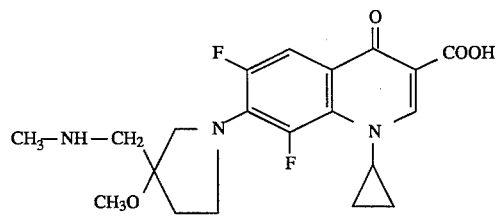

3-Methoxy-3-methylaminomethylpyrrolidine is reacted analogously to Example 1 and 1-cyclopropyl-6,8 -difluoro-1,4-dihydro-7-(3-methoxy-3-methylaminomethyl-1 -pyrrolidinyl)-4-oxo-3-quinolinecarboxylic acid of melting point 245°–247° C. (with decomposition) (recrystallized from dimethylformamide) are obtained.

EXAMPLE 21

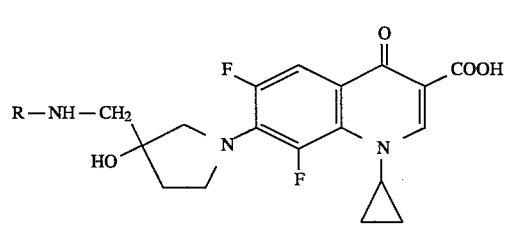

a) R = (CH3)3C—O—CO
b) R = H x HCl

1-Cyclopropy-6,7,8-trifluoro-1,4dihydro-4-oxo-3-quinoline carboxylic acid is reacted analoguosly to example 18:

a) 7-(3-tert.-Butoxycarbonylaminomethyl-3-hydroxy-1-pyrrolidinyl)-1-cyclopropyl-6,8-difluoro-1,4-dihydro-4-oxo-quinoline carboxylic acid.

Melting point: 199°–201° C. (decomposition)is obtained.

b) 7-(3-Aminomethyl-3-hydroxy-1-pyrrolidinyl)-1-cyclopropyl-6,8-difluoro-1,4-dihydro-4-oxo-3-quinoline carboxylic acid-hydrochloride.

Melting point: 269°–270° C. (decomposition) is obtained.

EXAMPLE 22

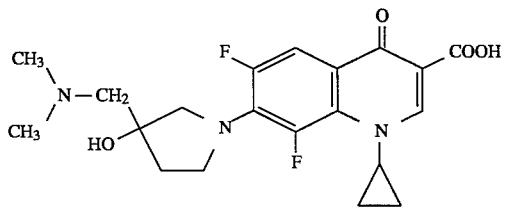

Following the description of example 1 the compound is reacted with 3-dimethylaminomethyl-3-hydroxy- 1-pyrrolidine and 1-cyclopropyl-6,8-difluoro-1,4-dihydro-7-(3-demithylaminomethyl-3-hydroxy-1-pyrrolidinyl)-4-oxo-3-quinoline carboxylic acid.

Melting point 203°–206° C. (decomposition) is obtained.

EXAMPLE 23

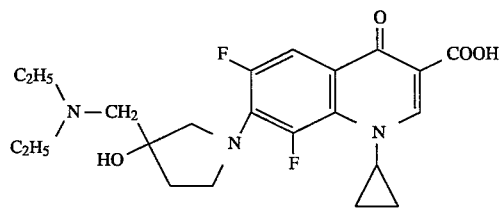

3-Diethylaminomethyl-3-hydroxy-pyrrolidine is reacted according to example 1, yielding 1-cyclopropyl-7-(3-diethylaminomethyl-3-hydroxy-1-pyrrolidinyl)-6,8-difluoro-1,4-dihydro- 4-oxo-3-quinoline carboxylic acid.

Melting point 202°–203° C. (decomposition).

EXAMPLE 24

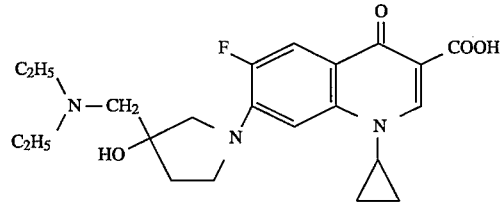

1-Cyclopropyl-6,7-difluoro-1,4dihydro-4-oxo-3-quinoline carboxylic acid is reacted according to example 1, yielding 1-cyclopropyl-7-(3-diethylaminomethyl-3-hydroxy-1-pyrrolidinyl)-6-fluoro- 1,4-dihydro-4-oxo-3-quinoline carboxylic acid.

Melting point 229°–232° C. (decomposition).

EXAMPLE 25

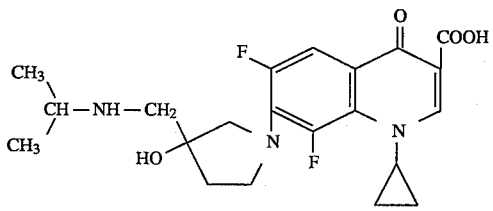

3-Isopropylaminomethyl-3-hydroxy-pyrrolidine is reacted according to example 1, yielding 1-cyclopropyl-6,8-difluoro-1,4-dihydro-7-(3-isopropylaminomethyl-3-hydroxy-1-pyrrolidinyl)-4-oxo-3-quinoline carboxylic acid.

Melting point 213°–214° C.

EXAMPLE 26

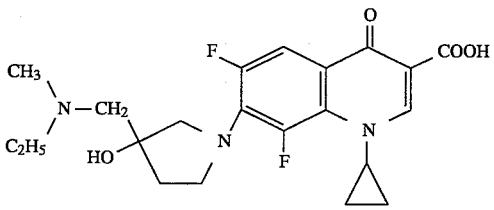

3-(N-ethyl-N-methyl-aminomethyl)-3-hydroxy-pyrrolidine is reacted according to expample 1, yielding 1-cyclopropyl-7-[3-(N-ethyl-N-methyl-aminomethyl)-3-hydroxy-1-pyrrodinyl]-6,8-difluoro- 1,4-dihydro-4-oxo-3-quinoline carboxylic acid.

Melting point 194°–195° C.

EXAMPLE 27

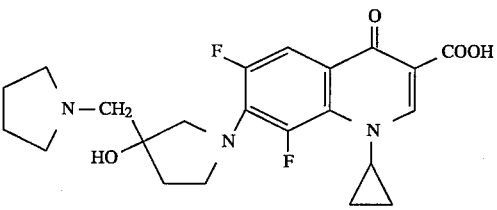

3-(1-Pyrrolidinylmethyl)-3-hydroxy-pyrrolidine is reacted according to example 1, yielding 1-cyclopropyl-6,8-difluoro-1,4-dihydro-4-oxo-7-[3-(1-pyrrolidinylmethyl)-3-hydroxy-1 -pyrrolidinyl-3-quinoline carboxylic acid.

Melting point 210°–215° C. (decomposition).

EXAMPLE 28

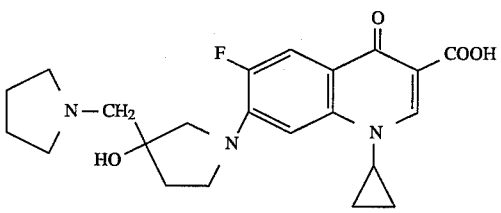

1-Cyclopropyl-6,7-diflouro-1,4-dihydro-4-oxo-3-quinoline carboxylic acid and 3-(1-pyrrolidinylmethyl)- 3-hydroxy-pyrrolidine are reacted according to example 1, yielding 1-cyclopropyl-6-fluoro- 1,4-dihydro-4-oxo-7[3-(1-pyrrolidinylmethyl)-3-hydroxy- 1-pyrrolidinyl]-3-quinoline carboxylic acid.

Melting point 229°–234° C. (decomposition).

EXAMPLE 29

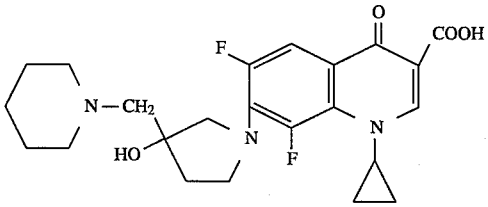

3-(4-Morpholinylmethyl)-3-hydroxy-pyrrolidine is reacted according example 1, yielding 1-cyclopropyl- 6,8-difluoro-1,4-dihydro-7[3-(4-morpholinylmethyl)-3-hydroxy-1-pyrrolidinyl-4-oxo-3-quinoline carboxylic acid.

Melting point 240°–242° C. (decomposition).

EXAMPLE 30

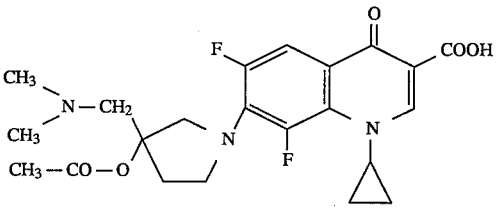

A mixture of 2.2 g (5 mmol) 1-cyclopropyl-6,8-difluoro-1,4-dihydro-7-(3-dimethylaminomethyl- 3-hydroxy-1-pyrrolidinyl)-4-oxo-3-quinoline carboxylic acid and 250 mg 4-dimethylaminopyridine in 80 ml of dry pyridine are treated with 2.5 ml of acetic acid anhydride. The mixture is stirred for 15 hours at room temperature. The organic solvents are removed from the suspension obtained, ice cold water is added to the residue and the precipitates are isolated by filtration washed with water and ethanol and dried.

Yield: 0.97 g (43% of theory) 7-(3-acetoxy-3-dimethylaminomethyl-1-pyrrolidinyl)-1-cyclopropyl6,8-difluoro-1,4-dihydro-4-oxo-3-quinoline carboxylic acid, melting point 215°–217° C. (decomposition) obtained.

EXAMPLE 31

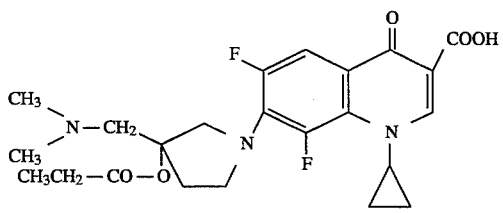

Analogously to example 30 the reaction with propionic acid anhydride yielded 1-cyclopropyl-7-(3-dimethylaminomethyl-3-propionyl-oxy-1-pyrrolidinyl)-6,8-difluoro-1,4-dihydro- 4-oxo-3-quinoline carboxylic acid.

Melting point 185°–187° C. (decomposition).

EXAMPLE 32

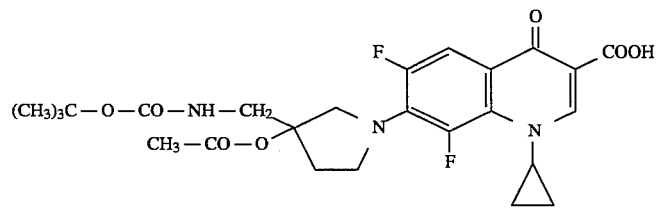

Analogously to example 30 7-(3-tert.-butoxycarbonylaminomethyl-3-hydroxy-1-pyrrolidinyl)-1-cyclopropyl-6,8-difluoro-1,4-dihydro-4-oxo-3-quinoline carboxylic acid are reacted with acetic acid anhydride, yielding 7-(3-acetoxy-3-tert.-butoxycarbonylaminomethyl-3-hydroxy-1-pyrrolidinyl)-1 -cyclopropyl-6,8-difluoro-1,4-dihydro-4-oxo-3-quinoline carboxylic acid.

Melting point 215° C. (decomposition).

EXAMPLE 33

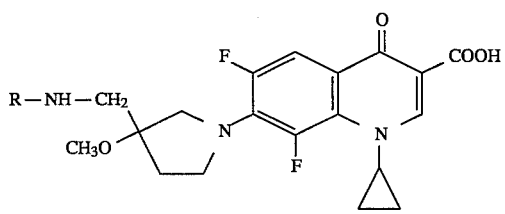

a) R = (CH₃)₃C—O—CO
b) R = H xHCl

Analogously to example 21 with 3-tert.-butoxycarbonylaminomethyl-3-methoxypyrrolidine (example W d)) following compounds are obtained:

a) 7-(3-tert.-butoxycarbonylaminomethyl-3-methoxy-1-pyrrolidinyl)-1-cyclopropyl-6,8-difluoro- 1,4-dihydro-4-oxo-quinoline carboxylic acid.

Melting point 185°–186° C. (decomposition), recrystallized from glykole monomethylether.

b) 7-(3-aminomethyl-3-methoxy-1-pyrrolidinyl)-1-cyclopropyl-6,8-difluoro-1,4-dihydro-4 -oxo-3-quinoline carboxylic acid-hydrochloride.

Melting point 223°–235° C. (decomposition).

Analogously to example 1, using 3-tert.-butylaminomethyl-3-hydroxy-pyrrolidine (example X b)) the following compounds are obtained:

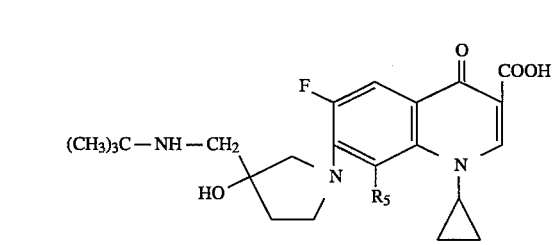

EXAMPLE 34 ($R^5$=H)

7-(3-tert.-butylaminomethyl-3-hydroxy-1-pyrrolidinyl)-1-cyclopropyl-6,8-difluoro-1,4 -dihydro-4-oxo-3-quinoline carboxylic acid.

Melting point 232°–233° C. (decomposition) (recrystallized from glycole monomethylether).

EXAMPLE 35 ($R^5$=H)

7-(3-tert.-butylaminomethyl-3-hydroxy-1-pyrrolidinyl)-1-cyclopropyl-6-fluoro-1,4-dihydro-4-oxo-3-quinoline carboxylic acid.

Melting point 278°–279° C. (decomposition) (recrystallized from glycole monomethylether).

EXAMPLE 36 ($R^5$=Cl)

7-(3-tert.-butylaminomethyl-3-hydroxy-1-pyrrolidinyl)-8-chlor-1-cyclopropyl-6-fluoro-1,4 -dihydro-4-oxo-3-quinoline carboxylic acid.

Melting point 251°–253° C. (decomposition) (recrystallized from glycole monomethylether/dimethylformamide).

EXAMPLE 37

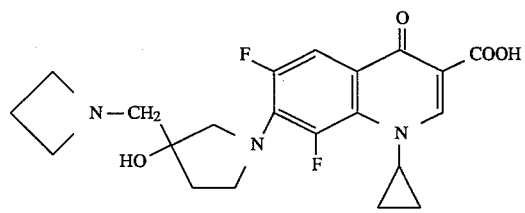

Analogously to example 1 with 3-azetidinylmethyl-3-hydroxy-pyrrolidine (example Y b)) 7-(-3-azetidinylmethyl-3-hydroxy-1-pyrrolidinyl)-1-cyclopropyl-6,8-difluoro-1,4-dihydro- 4-oxo-3-quinoline carboxylic acid is obtained.

EXAMPLE 38

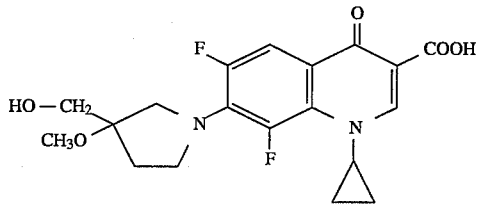

Analogously to example 1 with 3-hydroxymethyl-3-methoxy-pyrrolidine (example Z c)) 1-cyclopropyl-6,8-difluoro-1,4-dihydro-7-(3-hydroxymethyl-3-methoxy-1-pyrrolidinyl)-4-oxo-3-quinoline carboxylic acid.

Melting point 235°–236° C. (decomposition) (recrystallized from glycole monomethylether) is obtained.

EXAMPLE 39

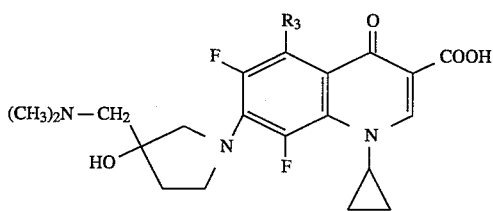

a) $R^3 = F$
b) $R^3 = NH_2$ a) Analogously to example 16, using 1-cyclopropyl-5,6,7,8-tetrafluoro-1,4-dihydro-4-oxo- 3-quinoline carboxylic acid 1-cyclopropyl-7-(3-dimethylaminomethyl-3-hydroxy-1-pyrrolindyl)-5,6,8-trifluoro-1,4-dihydro-4-oxo-3-quinoline carboxylic acid.

Melting point 225°–229° C. (decomposition) is obtained. The melting point of the respective hydrochlorid is 280°–286° C. (decomposition).

b) 2.5 g (5.9 mmol) of the product according to example 39 a are dissolved 25 ml pyridine and 25 ml saturated ethanolic amoniasolution is added. The mixture is heated during 12 hours in an autoclave to 125° C., and the organic solvents are thereafter removed in vacuo. From the residue the title compound is isolated by chromatography (SiO₂; dichloromethane-methanol-20% NH₃-solution=110:80:15).

Yield: 0.15 g 5-amino-1-cyclopropyl-7-(3-dimethylaminomethyl-3-hydroxy-1-pyrrolidinyl)- 6,8-difluoro-1,4-dihydro-4-oxo-3-quinoline carboxylic acid.

Melting point 192°–195° C. (decomposition).

FAB-mass spectra: positive m/e 423 ([M+H]⁺); negative m/e 421 ([M−H]⁻)

Analogously to example 1 the compounds of example 40 and 41 are obtained.

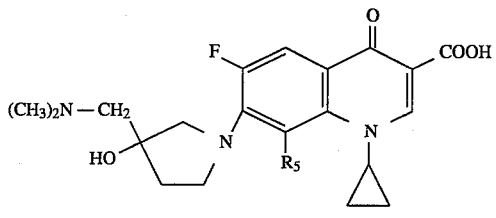

EXAMPLE 40 ($R^5$=H)

1-cyclopropyl-7-(3-dimethylaminomethyl-3-hydroxy)-6-fluoro-1,4-dihydro-4-oxo-3-quinoline carboxylic acid.

Melting point 240°–242° C. (decomposition) (recrystallized from dimethylformamide).

EXAMPLE 41 ($R^5$=Cl)

8-chloro-1-cyclopropyl-7-(3-dimethylaminomethyl-3-hydroxy)-6-fluoro-1,4-dihydro-4-oxo- 3-quinoline carboxylic acid.

Melting point 191°–194° C. (decomposition) (recrystallized from glycole monomethylether).

EXAMPLE 42

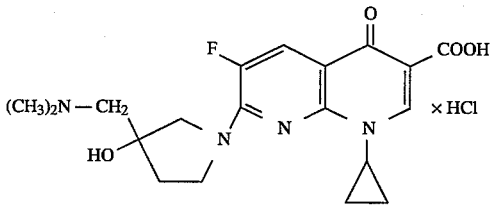

1.97 g (7 mmol) 7-chloro-1-cyclopropyl-6-fluoro-1,4-dihydro-4-oxo-1,8-naphthyridine- 3-carboxylic acid are dissolved in 21 ml acetonitrile and 2.0 g (14 mmol) 3-dimethylaminomethyl-3-hydroxypyrrolidine are added. The mixture ist stirred under a dry atmosphere for 12 hours at room temperature. The precipitate obtained is isolated and the title compound is obtained by chromatography (SiO₂; dichloromethane-methanol-17% NH₃ in water=30:8:1).

Yield: 2.2 g (81% of theory) 1-cyclopropyl-7-(3-dimethyl-aminomethyl-3-hydroxy-1-pyrrolidinyl)- 6-fluoro-1,4-dihydro-4-oxo-1,8-naphthyridine-3-carboxylic acid. 1.9 g of this compound are dissolved in 20 ml semiconcentrated hydrochloride acid, the volatile components of the solution are removed in vacuo, and the residue is taken up in ethanol. The unsoluble components are removed by filtration, and dried at 100° C. in vacuo.

Yield: 1.7 g (82% of theory) 1-cyclopropyl-7-(3-dimethylaminomethyl-3-hydroxy-1-pyrrolidinyl)- 6-fluoro-1,4-dihydro-4-oxo-1,8-naphthyridine-3-carboxylic acid-hydrochloride.

EXAMPLE 43

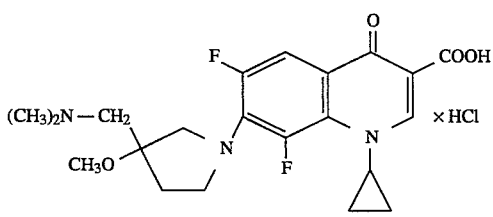

0.8 g of the product of example 20 is heated in a mixture of 25 ml 87% proof formic acid and 25 ml 37% proof aqueous formldehyde solution under reflux for 4 hours. From the yellow solution the volatile components are removed in vacuo, and from the residue the title compound is isolated by chromatography (SiO$_2$; dichloromethane-methanol=95:5> dichloromethane-methanol 20% NH$_3$ aqueous solution=2:4:1).

Yield: 140 mg 1-cyclopropyl-7-(3-dimethylaminomethyl-3-methoxy-1-pyrrolidinyl)-6,8-difluoro- 1,4-dihydro-4-oxo-3-quinoline carboxylic acid.

Melting point 232° C. (decomposition).

EXAMPLE 44

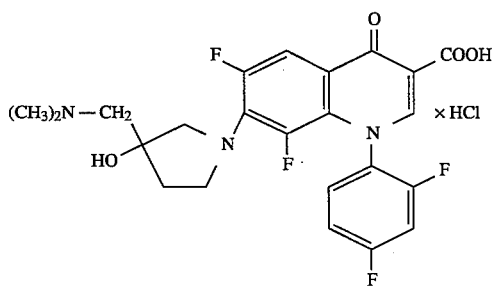

Analoguosly to example 16, using 1-(2,4-difluorophenyl)-6,7,8-trifluoro-1,4-dihydro-4-oxo- 3-quinolinecarboxylic acid the compound 1-(2,4-difluorophenyl)-7-(3-dimethylaminomethyl-3-hydroxy-1-pyrrolod inyl)-6,8-difluoro-1,4-dihydro-4-oxo-3-quinoline carboxylic acid-hydrochloride.

Melting point 275° C. (decomposition) is obtained.

EXAMPLE 45

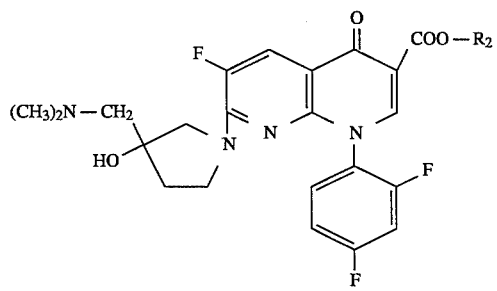

a) R = C$_2$H$_5$ b) R = H × HCl a) 1.91 g (5 mmol) 7-chlor-1-(2,4-difluorophenyl)-6-fluoro-1,4-dihydro-4-oxo-1,8 -naphthyridine-3-carboxylic acid-ethylester is dissolved in 20 ml acetonitril. 864 mg (6 mmol) 3-dimethylaminomethyl-3-hydroxy-pyrrolidine and 672 mg (6 mmol) 1,4 -diazabicyclo[2.2.21]octane are added, and the mixture is stirred for 4 hours at room temperature. Thereafter 20 ml of water are added, and the pH is adjusted to 9 with deluted NaOH. The precipitate is isolated by filtration, washed with water and dried in vacuo.

Yield: 1.66 g (68% of theory) 1-(2,4-difluorophenyl)-7-(3-dimethylaminomethyl-3-hydroxy- 1-pyrrolidinyl)-6-fluoro-1,4-dihydro-4-oxo-1,8-nophthyridine-3-carboxylicacid-ethylester.

Melting point 156°–158° C.

b) 1.51 g of the product of example 45 a is suspended in a mixture of acetic acid and 6n-hydrochloric acid (1:1), and the mixture is heated to reflux for 5 hours. The volatile constituents are removed in vacuo, the residue is taken up in water, the precipitates isolated by filtration and dried in vacuo.

Yield: 0.5 g (33% of theory) 1-(2,4-difluorophenyl)-7-(3-dimethylaminomethyl-3-hydroxy-1 -pyrrolidinyl)-6-fluoro-1,4-dihydro-4-oxo-1,8-nyphthyridine-3-carboxylic acid-hydrochloride.

Melting point 265° C. (decomposition).

It will be appreciated that the instant specification and claims are set forth by way of illustration and not limitation, and that various modifications and changes may be made without departing from the spirit and scope of the present invention.

What is claimed is:

1. A quinolonecarboxylic acid of the formula

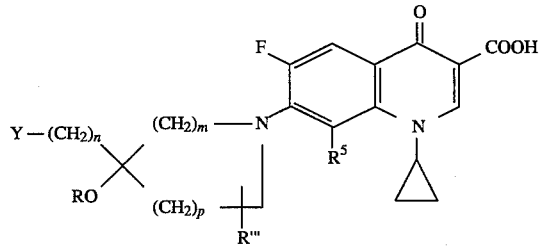

in which

P stands for 0 or 1 m stands for 1 or 2, where p+m together are 2 n stands for 1 or 2,

Y stands for

R stands for C$_1$–C$_3$-alkyl or C$_1$–C$_3$-acyl,

R' stands for hydrogen, C$_1$–C$_3$-alkyl, allyl or propargyl,

R" stands for hydrogen, C$_1$–C$_3$-alkyl or C$_3$–C$_6$ -cycloalkyl,

R''' stands for hydrogen or C$_1$–C$_3$-alkyl, and $R^5$ stands for fluorine, or a pharmaceutically utilizable hydrate, acid addition salt, alkali metal salt, alkaline earth metal salt, silver salt or guanidinium salt thereof.

2. A compound according to claim 1, of the formula

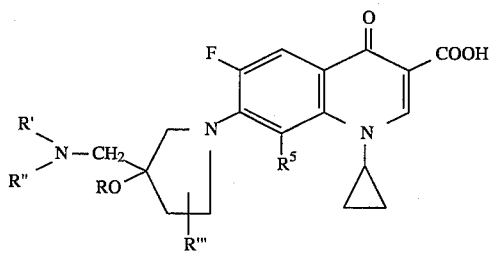

in which

R stands for $C_1$–$C_2$-alkyl or acetyl,

R' stands for hydrogen or $C_1$–$C_2$-alkyl,

R" stands for hydrogen or $C_1$–$C_2$-alkyl,

R'" stands for hydrogen or $C_1$–$C_2$-alkyl, and $R^5$ stands for fluorine, or a pharmaceutically utilizable hydrate, acid addition salt, alkali metal salt, alkaline earth metal salt, silver salt or guanidium salt thereof.

3. A compound according to claim 2, in which

R stands for methyl

R' stands for hydrogen or methyl,

R" stands for hydrogen or methyl

R'" stands for hydrogen or methyl, and $R^5$ stands for fluorine, or a pharmaceutically utilizable hydrate, acid addition salt, alkali metal salt, alkaline earth metal salt, silver salt or guanidinium salt thereof.

4. A compound according to claim 1, wherein R is $C_1$–$C_3$-alkyl.

5. A compound according to claim 1, wherein such compound is 1-cyclopropyl-6,8-difluoro-1,4-dihydro-7-(3-methoxy-3-methylaminomethyl- 1-pyrrolidinyl)-4-oxo-3-quinolinecarboxylic acid of the formula

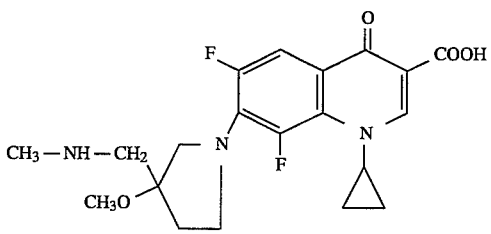

or pharmaceutically utilizable hydrate, acid addition salt, alkali metal salt, alkaline each metal salt, silver salt or guanidinium salt thereof.

6. An anti-bacterial composition comprising an antibacterially effective amount of compound according to claim 1 and a pharmaceutically acceptable diluent.

7. An anti-bacterial composition comprising an antibacterially effective amount of a compound according to claim 5 and a pharmaceutically acceptable diluent.

8. A method of combating bacteria in a patient which comprises administering to such patient an antibacterially effective amount of a compound according to claim 1.

9. A method of combating bacteria in a patient which comprises administering to such patient an antibacterially effective amount of a compound according to claim 5.

10. An animal growth-promoting composition comprising an edible carrier and an animal growth-promoting effective amount of a compound according to claim 1.

11. A method of promoting the growth of an animal which comprises administering to such animal growth-promoting effective amount of a compound according to claim 1 and a pharmaceutically acceptable diluent.

* * * * *

UNITED STATES PATENT AND TRADEMARK OFFICE
CERTIFICATE OF CORRECTION

PATENT NO. : 5,453,422
DATED : September 26, 1995
INVENTOR(S) : Petersen, et al.

It is certified that error appears in the above-indentified patent and that said Letters Patent is hereby corrected as shown below:

```
Title Page    [30] Foreign Application Priority Data:  After
                   " Feb 5, 1988 [DE] Germany... " delete-
                   " 38 02 478.6 " and substitute
                   -- 38 03 478.6 --
```

Signed and Sealed this

Sixteenth Day of January, 1996

Attest:

BRUCE LEHMAN

*Attesting Officer*    *Commissioner of Patents and Trademarks*